Figure 1:
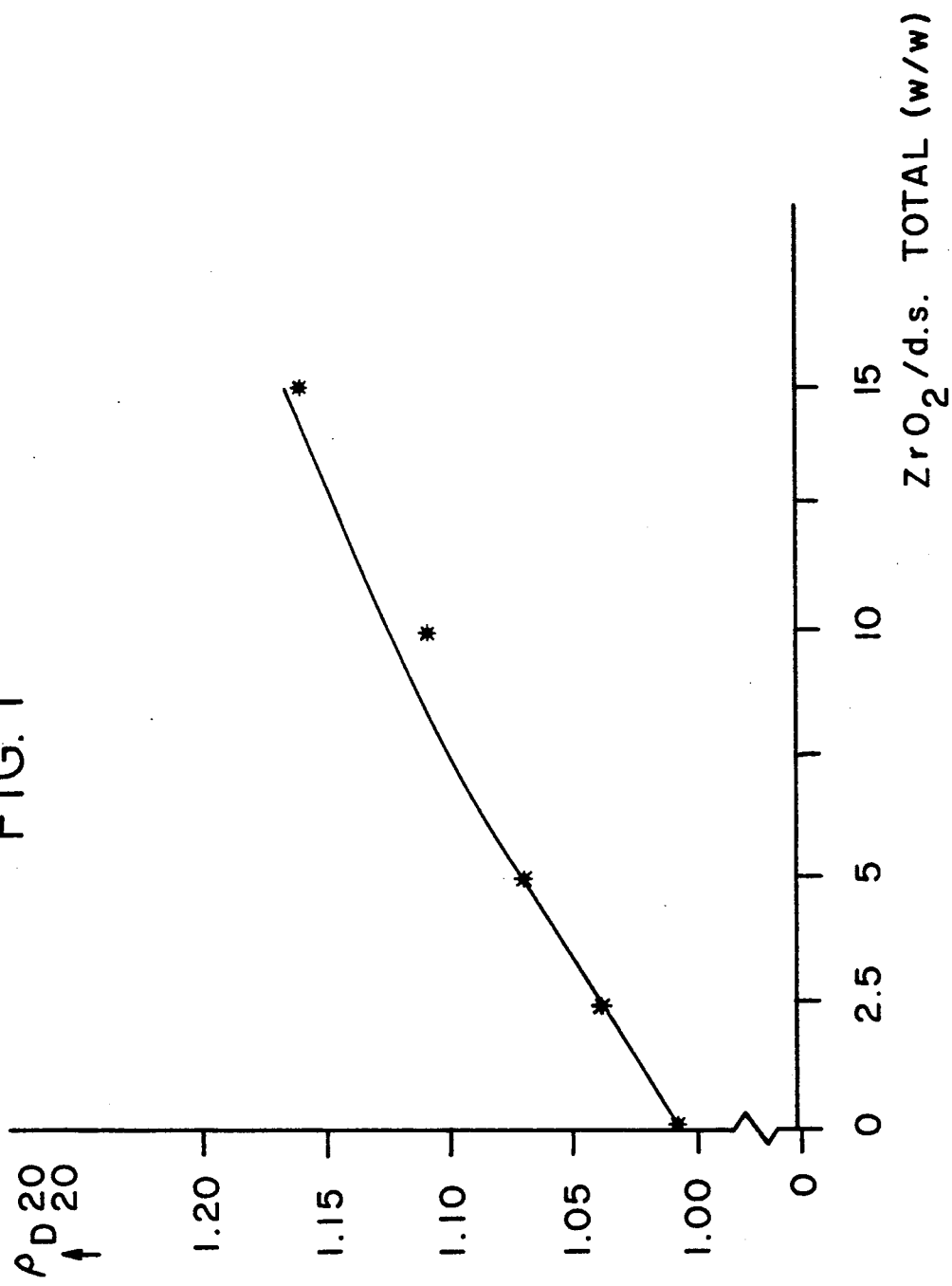

United States Patent [19]

Harder et al.

[11] Patent Number: 5,137,818
[45] Date of Patent: Aug. 11, 1992

[54] IMMOBILIZED BIOCATALYSTS

[75] Inventors: Abraham Harder, Berkel en Rodenrijs; Ben R. DeHaan, Rijswijk; Johannes B. Van Der Plaat, Leiderdorp, all of Netherlands; Marsha Cummings, Gastonia, N.C.

[73] Assignee: Gist-Brocades N.V., Delf, Netherlands

[21] Appl. No.: 547,868

[22] Filed: Jul. 2, 1990

Related U.S. Application Data

[63] Continuation-in-part of Ser. No. 88,849, Jul. 8, 1987, abandoned.

[30] Foreign Application Priority Data

Nov. 15, 1985 [EP] European Pat. Off. ........ 85-201883.7
Jun. 13, 1986 [EP] European Pat. Off. ........ 86-304578.7

[51] Int. Cl.$^5$ ................. C12N 11/02; C12N 11/12; C12N 11/04

[52] U.S. Cl. .................... 435/177; 435/174; 435/179; 435/180; 435/182; 435/240.22; 435/942; 435/161

[58] Field of Search ............... 435/174, 177, 179, 180, 435/182, 240.22

[56] References Cited

U.S. PATENT DOCUMENTS

| | | | |
|---|---|---|---|
| 4,163,691 | 8/1979 | Devos et al. | 435/182 |
| 4,287,305 | 9/1981 | Compere et al. | 435/176 |
| 4,337,313 | 6/1982 | Hershberger et al. | 435/182 |
| 4,338,401 | 7/1982 | Cremonesi | 435/182 |
| 4,411,999 | 10/1983 | Shigesada et al. | 435/177 |
| 4,459,312 | 7/1984 | Hartmeier | 435/181 |
| 4,546,078 | 10/1985 | Manecke et al. | 435/182 |
| 4,605,622 | 8/1986 | Hasegawa et al. | 435/182 |
| 4,647,536 | 3/1987 | Mosbach et al. | 435/177 |
| 4,798,786 | 1/1989 | Tice et al. | 435/177 |
| 4,803,168 | 2/1989 | Jarvis | 435/240.22 |

Primary Examiner—Herbert J. Lilling
Attorney, Agent, or Firm—Bierman and Muserlian

[57] ABSTRACT

Immobilized water-insoluble biocatalysts in particulate form comprise living cells, particularly yeast, dispersed in a cross-linked gelling agent. An enzyme, particularly amyloglucosidase, may be co-immobilized in the particles. These particles are prepared by suspending the living cells in an aqueous solution of a gelling agent, dispersing this suspension in a water immiscible organic liquid to form a suspension in the liquid of aqueous particles comprising the living cells and gelling agent, gelling the gel and cross-linking the gelling agent. It is found that when living cells such as microbial cells and especially yeast are immobilized in this way, that surprisingly, not only is their viability retained, but the ability of yeast cells to produce ethanol under continuous fermentation conditions is significantly improved. Specific strains of *Saccharomyces cerevisiae*, suitable for immobilization in this way, are described.

9 Claims, 9 Drawing Sheets

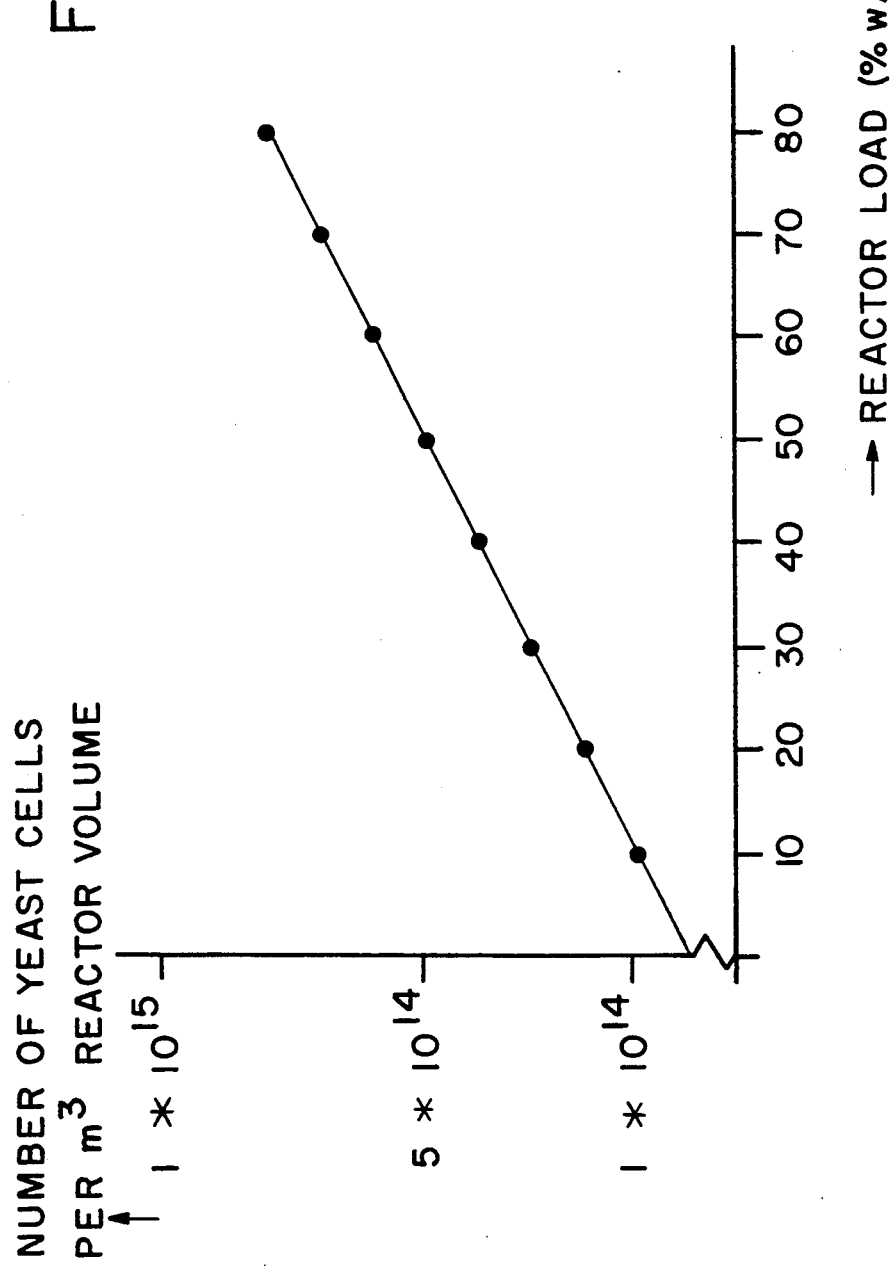

IMMOBILIZED BIOCATALYSTS

PRIOR APPLICATION

This application is a continuation-in-part of U.S. patent application Ser. No. 088,849 filed Jul. 8, 1987, now abandoned.

The present invention relates to novel immobilized water-insoluble biocatalysts in particulate form comprising living cells and to their preparation and use.

STATE OF THE ART

In U.S. Pat. No. 3,838,007 a process for preparing a water-insoluble enzyme composition in semi-solid or solid particulate form is disclosed by suspending a non-proteolytic enzyme in an aqueous solution of gelling protein, combining the mixture obtained with an organic liquid poorly miscible or immiscible in water to produce a suspension in particulate form, treating the resulting suspension to effect gelation of the gelling protein and contacting the resulting gelled protein particles with a cross-linking agent. The gelling protein which is preferably gelatin is essential to bring the enzymes into water-insoluble particulate form of desired sizes and it also stabilizes the enzyme. Organic liquids which are disclosed to bring about the particulate form of the aqueous enzyme-gelling protein solution are, inter alia, aliphatic alcohols with four or more carbon atoms such as butanol, esters of alcohols and lower fatty acids such as ethyl acetate, butyl acetate and ethyl propionate. Finally, several non-proteolytic enzymes are mentioned, which can be brought in insoluble particulate form. Said compositions in particulate form can be used in column and bed reactors for enzymatic reactions and are especially useful for those reactions in which the final product is not allowed to contain the enzyme employed.

It will be appreciated by people skilled in the art that living cells, for example cells of bakers' yeast (*Saccharomyces cerevisiae*), are rapidly killed by organic solvents of the type used in the method disclosed in U.S. Pat. No. 3,838,007. Several organic solvents have been reported to initiate autolysis in yeast. Ethyl acetate, for example, is used for the treatment of bakers' yeast to prepare crystalline cytochrome c, Nature 178 (1956), page 629 to 630, and $\beta$-fructofuranosidase, J. Bacteriol. 112 (1972), page 1346 to 1352.

Hough and Lyons, Nature 235 (1972) page 389, noted that the methods for insolubilization of enzymes by covalent linking were rather drastic for living organisms, so that they thought it highly unlikely that these living organisms would remain viable if used as supports. They then disclosed a technique for covalent coupling certain enzymes to living supports, viz. several strains of *Saccharomyces cerevisiae*, using titanium salts and other inorganic salts as coupling agents. This coupling technique was a modification of a technique originally disclosed by Barker et al., Process Biochem. 6, (1971), page 11.

In German Offenlegungsschrift No. 2,805,607, page 9, lines 13 to 17, reference was made to Processes Biochem. No. 7 (1972), page 9 to 12, in which it was proposed to entrap microorganisms in cellulose triacetate threads using toluene or methylene chloride as solvents. It was noted in said German Offenlegungsschrift that these solvents are very toxic, so that regeneration of the microorganisms by growing within the supporting matrix is hardly possible.

More recently, Haegerdal and Mosbach, Food Process Eng., Proc. Int. Congr., 2nd 1979 (Pub. 1980) 2, page 129 to 132, (cf. Chemical Abstracts 94 (1981) 119457k) described a co-immobilisate of baker's yeast with $\beta$-glucosidase, which was studied in a small column reactor for the production of ethanol from cellobiose. The enzyme was covalently bound to alginate and baker's yeast cells, were then co-entrapped with this preparation in an alginate gel, but neither an organic solvent nor a cross-linking agent was used with these living cells.

Calcium alginate has the drawback that it is unstable in the presence of phosphate ions or other chelating agents. In living cells phosphate salts are indispensable nutrients, so that such alginate supports are not suitable for use in most immobilized systems comprising viable cells.

European patent application EP-A-0,041,610 discloses co-immobilisates of yeast with enzymes, wherein the enzymes are coupled to living yeast cells capable of fermentation so as to surround them directly. These co-immobilizates are prepared by dewatering the yeast cells, rehydrating by means of an aqueous enzyme solution, adding an enzyme precipitating agent which does not affect the fermentation of the yeast cells and preferably subsequent addition of a cross-linking agent. Neither an organic solvent nor a dispersing agent was used in the preparation of these co-immobilizates. The co-immobilizates are unsuitable for use in column reactors and the like, because they lack a supporting matrix.

European patent application No. EP-A 0,350,374 discloses microorganisms which are included in a gel which is subsequently dehydrated by placing droplets of the microorganism/gel suspension in a hydrophillic solution containing a low molecular weight polyol or saccharide. After this dehydration step, the resulting particles may be further dried via lyophilization or in a fluidized bed process or again in a dehydrating salt solution. There is no mention of placing the droplets of the microorganism/gel suspension in an organic solvent. Moreover, the gel is not cross-linked either before or after dehydration step.

All these references teach away from the use of organic solvents and especially solvents of the type of toluene, butanol, butyl acetate and ethyl acetate in preparing immobilized living cells compositions which retain their fermentation and multiplication capability.

OBJECTS OF THE INVENTION

It is an object of the invention to provide immobilized water-insoluble biocatalysts in particulate form of desired sizes comprising living cells, which can be used for various purposes, for example in column fillings, fluidized bed reactors and stirred tank reactors.

It is another object of the invention to provide a process for the preparation of the said immobilized water-insoluble particles under fairly mild conditions (i.e. the conditions within the particles, such in contrast with the surrounding organic solvents in which the suspensions are extruded), so that a substantial amount of the living cells may survive or can be regenerated after immobilization.

It is a further object of the invention to provide immobilized water-insoluble biocatalysts which have a long shelflife, as well as having good mechanical strength and stability to allow for their long term use (at least 12 to 24 months) in continuous fermentation processes without the loss of either viability or activity of the immobilized cells or enzymes which may optionally be co-immobilized therein. Such long-term usage of live biocatalysts has long been a goal of those skilled in the art, yet up until now has never been realized.

These and other objects and advantages of the invention will become obvious from the following detailed description.

THE INVENTION

After extensive research and experimentation, it was surprisingly found that the viability of living cells and in particular of living microbial cells, for example yeasts, is not adversely affected when the living cells are brought into contact with an organic liquid poorly miscible or immiscible with water if the living cells are suspended in an aqueous solution of a gelling agent.

Accordingly, the present invention provides an immobilized water-insoluble biocatalyst in particulate form comprising living cells dispersed in a cross-linked gelling agent.

The term "living cells" used in this specification is to be understood as cells having the compatibility to carry out a wide range of metabolic (or anabolic) reactions which are only possible if said cells keep their structural entity. Examples of such reactions are generation of energy (ATP), recycling of cell constituents, and cell multiplication.

The term "particulate form" used in this specification should be interpreted in a broad sense. The particulate form may be a form of spherical or almost spherical particles, but, although the specification generally refers to those spherical or almost spherical particles, the particulate form may also be the form of, for example, fibers, e.g. extruded fibers, a cast film, a coating of vessels and impregnated tissue or paper. In general, "particulate form" means a form of the composition according to the invention of defined desired sizes.

The term "gelling agent" used herein means an agent of which an aqueous solution may be transformed into a solid or semi-solid state by special treatment, e.g. by cooling when gelatin or agar is used. Suitable gelling agents for the purpose of the invention are, for example, gelatin, mixtures of a gelling polycarbohydrate such as agar, and a polymer containing free amino groups such as chitosan, capable of being cross-linked with a suitable bi- or polyfunctional cross-linking agent, and mixtures of gelatin and such compounds. Gelatin and mixtures of gelatin and chitosan are the preferred gelling agents.

Examples of suitable cross-linking agents for the purpose of this invention are, for example, glutaric dialdehyde which is preferred and tannic acid Suitable living cells for the immobilized water-insoluble biocatalysts according to the invention are, for example, microbial cells and cells of animals and higher plants. Among the suitable living microbial cells which are preferred, are yeasts and bacteria, such as species of e.g. *Saccharomyces cerevisiae* (baker's yeast) and *Saccharomyces bayanus* (Red Star Cantarelli Champagne variety) and species of Acetobacter (e.g. *Acetobacter pasteurianum*), Clostridium (e.g. *Clostridium butyricum, Clostridium thermocellum* and *Clostridium acetobutylicum*), Klebsiella Rhizopus (e.g. *Rhizopus oryzae*), Bacillus (e.g. low protease producing strains of *Bacillus laevolactis* and Lactobacillus (e.g. *Lactobacillus bavaricus* and *Lactobacillus delbruekii*. Suitable living plant cells are, for example, cells belonging to the species *Tagetes minuta*.

In accordance with a further aspect of the present invention, the immobilized water-insoluble biocatalysts may also comprise one or more enzymes, particularly a non-proteolytic enzyme. When an enzyme is incorporated in the biocatalyst, it must, of course, be compatible with the living cells and the gelling agent. Examples of enzymes which may be included in the biocatalysts of the invention are, for example, amyloglucosidase, lactase, maltase, amylase, glucose isomerase, pullulanase, invertase, lipase, esterase, glucose oxidase and dehydrogenase. Mixtures of enzymes may also be employed.

In particular, one or more enzymes may be selected for co-immobilization to allow for the use of complex carbohydrates such as starches as the fermentable substrate in place of simple sugars such as glucose. The enzyme(s) selected should be capable of cleaving monosaccharide subunits which in turn are fermented via the immobilized cells to produce the desired product. In this manner, the level of monosaccharides present in the fermentation medium is kept low, thus reducing he occurrences of contamination (sterility) problems which can plague long-term fermentation processes. Preferred fermentable substrates are liquefied starch, dextrins, cellobiose and partially hydrolyzed cellulose feed stock. Enzymes which are suitable for such use are selected for their compatibility with the fermentable substrate. Exemplary enzymes are amyloglucosidase, α-amylase (especially of fungal origin), pullulanase, acid amylase, xylanases, hemicellulases, β-glucosidase and other cellulases.

Proteolytic enzymes may also be used under certain conditions, which will be clear to those skilled in the art. It has been found that the immobilized biocatalysts of the present invention are surprisingly resilient to the expected adverse effects of proteolytic enzymes such as decomposition and physical instability. Although the presence of proteases may cause the beads to swell, upon removal of the beads from the protease environment, the beads demonstrate a remarkable ability to return to their normal shape and size without significant detrimental effects to their performance as biocatalysts. The beads of the present invention have been found to be stable in 10,000 Units/ml neutral protease (HUT units) at pH 5.5 for a period of up to 7 days.

In accordance with still another aspect of the invention, the immobilized water-insoluble biocatalysts may comprise two or more types of living cells, optionally in conjunction with one or more enzymes.

The immobilized water-insoluble biocatalysts in particulate form according to the invention are especially useful in column reactors, for example fluidized bed reactors, or in stirred tank reactors, for continuous biocatalytic reactions. Suitably, these biocatalysts can be used for the conversion of certain carbohydrates, such as oligosaccharides from liquefied starch into ethanol, the conversion of lactose (for example in whey) into lactic acid or ethanol and the conversion of cellobiose into acetic acid, itaconic acid or citric acid. Suitable immobilized water-insoluble biocatalysts according to the invention are those which comprise *Saccharomyces cerevisiae* or *Saccharomyces bayanus* to produce glycerol with ethanol as by-product, or in conjunction for example with lactase to convert whey into ethanol, or with *Zymomonas mobilis* to produce continuously and rapidly ethanol from liquefied starch. Preferred immobilized water-insoluble biocatalysts are those which comprise *Saccharomyces cerevisiae*, optionally in conjunction with one or more amylolytic enzymes, in particular amyloglucosidase. Such a combination is particularly useful in fermentation to produce ethanol from liquefied starch, e.g. dextrin, and in the production of low-calorie beer. Other suitable biocatalysts according to the invention are immobilized organisms which produce D-lactic acid (e.g. Bacillus species) or L-lactic acid (e.g. Lactobacillus and Rhizopus species), immobilized organisms producing mono-oxydases to convert hydrocarbons to ketones or acids (e.g. Clostridium, Klebsiella and Aerobacter species), immobilized ligninase producing organisms for treatment of sulfite liquors from production of paper (e.g. Coriolus, Phanerochaete, Sporotrichum and Streptomyces species), immobilized organisms which produce enzymes that catalyze specific reactions in the preparation of certain types of pharmaceutically active compounds (e.g. Curvularia, Mycobacterium and Pseudomonas species, useful e.g. in the preparation of steroids and optically active isomers), immobilized Acetobacter species for the production of acetic acid from starch or glucose, and immobilized hybridoma cells for the production of monoclonal antibodies.

According to another aspect of the invention, the aforesaid immobilized water-insoluble biocatalysts may be prepared by a method comprising the following steps:

(a) suspending the living cells in an aqueous solution of a gelling agent, (b) combining the mixture so obtained with an organic liquid poorly miscible or immiscible in water to form a suspension in the organic liquid of aqueous particles comprising the living cells and the gelling agent, (c) treating the suspension to gel the gelling agent in the particles, (d) treating the particles obtained in step (c) with a bi- or polyfunctional cross-linking agent to cross-link the polymers present in the particles, and (e) removing at least part of the water from the particles obtained in step (d).

The method according to the invention has many advantages which makes it highly attractive for industrial use. For example, it is simple, so that the process can be accurately controlled. The particles obtained are evenly divided and homogenous. They are usually in semi-solid or, more preferably, in solid form. By extruding in butyl acetate or toluene, the immobilization method is also aspectic. Finally, the method is relatively inexpensive.

The gelling agent is preferably gelatin or a mixture consisting essentially of gelatin and chitosan, which also stabilizes any enzymes incorporated in the biocatalyst.

The mixture of living cells, enzyme and gelling agent in particulate form is preferably formed by suspending the living cells and, optionally, the enzyme in an aqueous solution of the gelling agent and combining this mixture with an organic liquid poorly miscible or immiscible with water so that the particulate form is obtained, and treating the resulting suspension in particulate form in such a way that gelation of the gelling agent is achieved, such as by cooling when gelatin is the gelling agent. The combining of the mixture containing the living cells, the optional enzyme(s) and the gelling agent with the organic liquid may be carried out by mixing under controlled agitation or by submerged spraying of the mixture of the living cells, the enzyme(s) and the gelling protein into the organic liquid. The latter procedure may be performed in a vertical column in which the particles formed are moving downward in the organic liquid which may contain the cross-linking agent.

The cross-linking of the mixture of the living cells, the optional enzyme and the gelling agent may be carried out by separating the mixture in particulate form from the organic liquid and treating it with the cross-linking bi- or polyfunctional agent. Alternatively, in some cases, for example with Clostridium cells, the mixture in particulate form suspended in the organic liquid may be treated with the said agent. When it is desired to incorporate an enzyme in the biocatalyst, the enzyme maybe introduced into the gelled suspension during the cross-linking step. If desired, the immobilized living cells may then be reactivated and grown.

The particles obtained after the cross-linking step are dried, so that they can be conveniently stored and packed. The drying or "dewatering" step comprises removing at least part of the water from the cross-linked particles by means of osmotic shrinking in a hydrophillic solvent such as acetone and/or via other dewatering means such as in a fluidized bed drier. Dewatering provides compact, spherical beads of uniform size and density which further have improved durability and mechanical strength The dewatered beds are thus resistant to damage caused by, inter alia, abrasion from continued contact with other substances inside the fermenter.

In a comparative test of abrasion tolerance between dewatered beads and beads identically prepared but not dewatered after cross-linking, the dewatered beads were unaffected by abrasive action whereas at least 60% of the non-dewatered beads were destroyed in each test.

Until now, it was expected that such compact particles would lack elasticity and that the biocatalysts would simply fill with cells and either break apart or the cells would cease multiplying and eventually die.

Surprisingly, however, the dewatered particles still have sufficient elasticity for the opening of pores in the cross-linked matrix. These pores allow the viable cells to grow and function normally within the cross-linked matrix, while the previous generations of cells are broken down and "sloughed off" through the pores.

The increased strength and durability of the particles, together with the fact that the immobilized cells are able to remain viable and function normally within the cross-linked matrix provide biocatalysts which are capable of long-term use (at least 12–24 months) in continuous fermentation processes. Before use, the particles are generally rehydrated and the immobilized living cells are optionally grown.

The mixture of living cells, enzyme(s) and gelling agent which is used in the process as a starting material may be prepared by suspending the living cells and, optionally, the enzyme(s) in an aqueous solution of gelling agent. The temperature of the aqueous gelling solution should be such that an active mixture is obtained in a liquid form. Therefore, a temperature of about 25° C. to about 40° C. is preferred with a maximum temperature depending on the thermotolerance of the viable cells used.

The gelatin in the solution is dependent on the specific gelatin used and may vary within limits of about 0.1 to about 25% by weight based on the water used, preferably within limits of about 5 to 10% by weight. The concentration of living cells and enzyme(s) depend on the purpose for which the insolubilized biocatalyst is to be used as well as on the activity thereof. When a mixture of gelatin and chitosan is used, the chitosan concentration may vary within limits of about 0.05 to about 10% by weight based on the water used, preferably within limits of about 0.1 to about 2% by weight. The pH of the solution is preferably that at which the cells possess their greatest stability under the circumstances involved, but, as gelatin is also present, the pH should be within limits of about 2 and 12, preferably within 3 to 10 in order to allow the gelatin to gell. For other gelling agents, the pH range may differ.

During the preparation of the mixture of living cells, enzyme and gelling agent, stabilizers may be added which in addition to the gelling agent, stabilize the living cells and/or the enzymes when present. It is noted that basically also cold water might be used instead of an organic liquid, but it has been found that this method does not lead to satisfactory results. Examples of stabilizers useful in the process according to the invention are sorbitol, glycerol, non-metabolisable substrates for the living cells and the enzymes used.

The organic liquid used to bring about the particulate form of the aqueous solution or suspension of living cells, enzyme and gelling agent is an organic liquid poorly miscible or immiscible in water. Examples of suitable organic liquids are aliphatic alcohols with four or more carbon atoms, e.g. alkanols such as butanol; esters of alcohols and lower fatty acids, e.g. $C_{1-4}$ alkanoic acids such as ethyl acetate, butyl acetate and ethyl propionate, branched or straight chain aliphatic hydrocarbons such as paraffin oil, petrol and petroleum ether, aromatic hydrocarbons such as benzene and its chlorinated hydrocarbons such as methylene chloride and trichloethylene, and mixtures of two or more of the above-mentioned liquids. Of these, butyl acetate is preferred, inter alia because of available simple and economically advantageous recovery procedures.

Types of agitation used during the combining of the aqueous living cells-optional enzyme-gelling agent mixture and the organic liquid and the cooling operation (when gelatin is used) of the resulting suspension may be any one resulting in a division of the aqueous living cells-optional enzyme-gelling agent mixture into particles of the desired sizes. The sizes obtained depend on the intensity of agitation, the difference in specific gravities of the liquids, the surface tensions and viscosities of the liquids, and in some cases the rate of cooling, the temperature and the concentration of the intial aqueous living cells-enzyme-gelling agent solution or suspension. Generally, stirring is sufficient but other methods such as spraying the living cells-enzyme-gelling agent mixture into the organic liquid to form the suspension may be used. Cooling of the living cells-enzyme-gelatin mixture in the organic liquid, e.g. down to about 10° C. or lower and even below the freezing point of the said mixture, may be applied simultaneously with or after the formation of the suspension of the mixture in the organic liquid, and cooling may be carried out quickly or slowly.

The cross-linking step is carried out with a bi- or polyfunctional cross-linking agent forming covalent bonds with the amino groups containing polymers. Examples of suitable bifunctional cross-linking agents are glutaric dialdehyde and tannic acid.

An embodiment of the invention involves dehydration of the particles, before the cross-linking step. The dehydration reduces the sizes of the particles obtained, and an improvement of the cross-linking reaction is achieved when these shrunken particles are brought into an aqeous solution of the bi- or polyfunctional cross-linking agent.

The dehydration step is preferably carried out by osmotic shrinking of the particles, for example with sorbitol or glycerol. The cross-linking bi- or polyfunctional cross-linking agent may be added to this liquid or applied to the particles after the dehydration step. The dehydration step may be applied after separation of the particles from the organic liquid used for the suspension step.

Insoluble fillers may be added to the cells-optional enzyme-gelling agent mixture employed in the process as they may improve the physical properties of the final particulate form. Examples of suitable insoluble fillers are finely divided silicates or silicon oxides such as KETJENSIL (a synthetic silicon oxide), HYFLO, DICALITE, diatomaceous earth, etc.

The immobilized biocatalysts according to the invention may also be coated with relatively heavy materials, e.g. zirconium oxide powder, to give the particles more weight, so that a higher superficial liquid rate can be obtained in fluidized bed reactors, resulting in higher oxygen concentration.

Finally, the cells-optional enzyme-gelling agent parparations obtained in particulate form by the process are preferably washed. Examples of suitable washing liquids are water or buffered solutions having a pH depending on the biologically active substance. Afterward, drying or dewatering of the preparation in particulate form is performed.

The dewatering step comprises the removal of at least part of the water content from the immobilizates, preferably by means of osmotic shrinking or by other drying means such as in a fluidized bed drier. Dewatering may be carried out up to eight hours after cross-linking, but preferably within an hour of cross-linking.

Osmotic shrinking is performed by placing the cross-linked beads in successive solutions, each having increasing concentration of a hydrophillic agent such as acetone. Other useful hydrophillic solvents for osmotic shrinking include methanol, ethanol, propanol, isopropanol, methyl ethyl ketone, ethyl methyl ether, diethyl ether, xylene, benzene or toluene.

Dewatering in acetone is preferred since this allows for cross-linking to continue as the beads shrink, providing a uniform, spherical product with good mechanical strength, i.e. abrasion resistance, and within which, upon rehydration, the immobilized microorganisms and optionally co-immobilized enzymes have good viabilities.

After dewatering, the beads may optionally be rinsed with water to remove excess acetone from the surface of the beads. In a preferred embodiment, the dewatered beads may then be further dried, for example in a fluidized bed drier, or may be rehydrated for use.

The cross-linked beads typically contain 2 to 10% dry matter before dewatering and 15 to 95% dry matter after dewatering. Dewatering by osmotic shrinking yields a product having between 15 to 50% dry matter content. In a preferred embodiment, the beads will contain between 18 to 45% dry matter after dewatering by osmotic shrinking.

Dewatering in a fluidized bed drier provides a product containing up to 95% dry matter. Preferably, the catalysts dried via the fluidized bed process will have a dry matter content within a range of 80 to 85%, thus providing optimal shelf life for the biocatalysts.

Dewatering is important for the final strength of the biocatalysts after rehydration as well as to avoid destabilization during storage. The dried biocatalysts of the present invention demonstrate good shelf life, yet without loss of activity of either the immobilized microorganism or of the optionally co-immobilized enzyme.

The percent dry matter is calculated by heating 15 grams of beads in a convection oven at 104° C. for 1 hour. The beads were weighed out in tared aluminum pans which had previously been heated to 104° C. for a minimum of 1 hour and then cooled to ambient temperature in a desiccator. After the beads were weighed, the pans were returned to the oven. After drying, the pans containing the beads were cooled to ambient temperature in a desiccator before weighing. Dry matter was calculated as follows:

$$\frac{\text{Final Weight} - \text{Tare Weight}}{\text{Original Weight} - \text{Tare Weight}} \times 100.$$

The gelling agent used in the invention such as gelatin is a polyelectrolyte which possibly influences the apparent pH optimum of any enzyme present, i.e. the pH where the enzyme exhibits its highest activity. In addition, other compounds influencing the apparent pH optimum of the enzyme may be included in the particles such as other polyelectrolytes, examples of which are protamine sulfate and polyacrylic acid, thus adapting the apparent pH optimum of the living cells-enzyme gelling agent particles to their future purpose for instance.

One of the practical problems encountered in the immobilization of yeast is that the fermentation characteristics of yeast when used conventionally change in an unpredictable manner when the yeast is immobilized and that desirable fermentation characteristics that are observed under conventional fermentation conditions are not necessarily retained when the same yeast is immobilized. It is also found that the fermentation characteristics of yeast vary in an unpredictable manner depending upon when the yeast is used in batch fermentation or continuous fermentation.

There is considerable interest in the use of continuous fermentation by the brewing industry and much research and development work is directed towards the production of immobilized yeasts that can be used in continuous fermenters for prolonged periods of time. The problems that arise concern, on the one hand, the physical integrity of the immobilized yeast over prolonged reaction periods and also the capacity of the yeast to produce, over the prolonged reaction periods from the desired sugar feed stock, ethanol at an acceptably high and acceptably constant concentration. A further problem that is encountered during continuous fermentation is that of heat generated in the bed of immobilized yeast. Many yeast which are of interest in the brewing industry perform very satisfactorily in batch fermentation but the same yeasts, when used in continuous bed fermenters become subject to thermal problems that adversely affect their performance. This in turn necessitates the provision of complex and expensive cooling mechanisms for the continuous bed fermenters.

In an attempt to identify classes of yeast that might be particularly suited to immobilization and use in continuous fermentation, we have screened a large variety of yeasts said to be thermophilic or, perhaps better, thermotolerant. The thermophilicity of a yeast appears from its capability of sustained growing in batch culture over several generations (at least 4 and 5) at a temperature in excess of 40° C., usually between 40° and 44° C. The thermophilicity of a yeast was assessed by a test in which it was grown on a defined medium at temperatures of at least 40° C. and the extent of growth determined by optical density readings. The procedure adopted was as follows.

The test yeast cultures were grown in an aqueous medium comprising 1% w/v bacto yeast extract, 2% w/v bacto peptone and 2% w/v glucose, hereinafter referred to as YEPD, that is yeast extract peptone dextrose. The test yeasts were pre-grown on a YEPD medium at 32° C. and then inoculated at a rate corresponding to 150 mg yeast dry matter per liter of stationery cells. The culture was grown for 16 hours at 42.5° C. and yeast cell growth determined by optical density readings. A yeast giving an optical density reading of at least 2.5 times greater than the optical density reading obtained for bakers' yeast 2103 Ng (CBS 6131) grown under identical conditions is regarded as thermophilic and, in this specification a thermophilic yeast is one meeting this optical density reading definition.

With these objectives in mind we have screened various thermotolerant yeasts which also have improved ethanol tolerance with a view to identifying strains that would be sufficiently thermophilic for immobilization in accordance with the present invention and use in continuous fermentation.

One such yeast that has emerged from our screening tests is one originally designated *Saccharomyces anamensis* which was first described in 1913. Subsequent workers have decided that this yeast is not a distinct species of Saccharomyces but is, in fact, a variant of *Saccharomyces cerevisiae* and the identity between *S. anamensis* and *S. cerevisiae* is set out in the first and second edition of Lodder and Kreger van Rij, The Yeasts, North Holland Publ. Co., Amsterdam, and in the subsequent editions by Kreger van Rij, published by Elsevier.

We have examined samples of *S. cerevisiae var. anamensis*, obtained from IFO, Osaka, Japan, under deposit number IFO 0203 and find, to our surprise, that its ability to ferment for example glucose, changes in an unexpected and very favorable manner when it is immobilized in accordance with the present invention. In our screening tests, the strain IFO 0203 was compared in various tests with a conventional baker's yeast, strain 227 Ng, sold in the United Kingdom, under the name Fermipan "red" by British Fermentation Products Ltd. (Fermipan is a Registered Trade Mark). We found that IFO 0203 was positive while 227 Ng was negative in our thermophilicity test at temperatures of 40° C. and above. In a further test to determine the amount of ethanol produced in six hours at 37° C., IFO 0203 produced 2.67% v/v while under the same conditions, 227 Ng produced substantially the same at 2.54% v/v.

A comparison was also made between the two strains of yeast in batch fermentation at high initial cell density when it was found that IFO 0203 could produce 15% v/v ethanol in the first 16 hours and 16.5% after 24 hours while, under the same conditions, 227 Ng could produce 18% ethanol in the first 16 hours and 18.5% ethanol in 24 hours. These tests were carried out under conditions such that fermentation did not cease as a result of lack of fermentable sugar.

A further comparison between the strains has been made to determine the so called D-value of the sugar. This is a concept introduced in East German Patent publication DD 216,480-A and identifies as alcohol tolerant yeasts having a D-value greater than 25 seconds. The D-value is the time in seconds required to kill 90% of the yeast cells when subjected to a temperature of 58° C. Yeasts with a D-value of less than 25 seconds are regarded as alcohol sensitive. In this test, IFO 0203 had a D-value of 50 seconds while 227 Ng had a value of 26 seconds, both being regarded as alcohol tolerant by this test.

On the basis of the various comparative tests described above based on conventional fermentation, there was no reason to suppose that there would be any significant difference in performance between the two strains of yeast when immobilized in accordance with the present invention and used in continuous fermentation. However, when this comparison was carried out, it was found, most surprisingly, that there was a very significant improvement in the performance of IFO 0203. When 227 Ng was coimmobilized with amyloglucosidase in accordance with the present invention and the particulate material loaded into a column which was continuously fed with a dextrin feed stock and an ethanol producing product stream continuously withdrawn, it was found that the product stream contained 8.5–9.5% v/v ethanol when the fermentation achieved its steady state running. When the same procedure was repeated with strain IFO 0203, an ethanol level of 11–12% was achieved and maintained for up to six months.

Our investigations on strain IFO 0203 show that some changes have occurred in the fermentation ability of the strain as reported by the original isolators of the strain and as reported in the first edition of Lodder in that, contrary to the published properties, we found that the IFO 0203 strain with which we have carried out the experiments described above will not ferment maltose. This suggests to us that mutation has ocurred since the original material was deposited and we have deposited the IFO 0203 strain of *S. cerevisiae* which will not ferment maltose on May 7, 1986 with the Central Bureau voor Schimmelcultures, Oosterstraat 1, 3742 SK Baarn, Netherlands where it has been given the deposit number CBS 252.86.

Additionally, we have investigated artificial mutant strains of strain IFO 0203 (CBS 252.86). We have attempted to mutate this strain by pulsing the yeast cells with known mutagens at sub-lethal doses. Mutagens we have used include sodium nitrite and ethyl methane sulfonate. One particular mutant, obtained by pulsing strain IFO 0203 with sodium nitrite and ethyl methane sulfonate has been found to show certain properties superior to even those of its parent strain. We have designated this mutant strain 2490-KI13 and we have also deposited the mutant strain 2490-Ki13 on May 7, 1986 with Central Bureau voor Schimmelcultures where it has been given the deposit number CBS 253.86. For brevity, we will prefer to this deposited mutant strain as mutant strain 13. Mutant strain 13 comprises a further embodiment of the present invention.

Mutant strain 13 has been subjected to the various comparative tests described above for parent strain IFO 0203. In the thermotolerant growth tests, mutant strain 13 was found to be less thermotolerant than its parent strain CBS 252.86 but rather more tolerant than 227 Ng. Optical density readings were made using a Klett-Summerson densitometer with a 66 filter and 3 independent readings were averaged to give the following results:

| STRAIN | 40° C. | 41.5° C. | 42.5° C. |
|---|---|---|---|
| IFO-0203 (CBS 252.86) | 408 | 357 | 345 |
| Mutant strain 13 (CBS 253.86) | 383 | 338 | 305 |
| 227 Ng | 325 | 113 | 100 |
| 2103 Ng (CBS 6131) | 171 | 149 | 99 |

In the conventional fermentation at 37° C., mutant strain 13 produced 3.61% v/v ethanol compared to 2.67% v/v for CBS 252.86 and 2.54% for 227 Ng.

In the test for determining alcohol production after 16 and 24 hours, mutant strain 13 produced only 13.25% v/v alcohol in 16 hours and 15.5% in 24 hours, being out-performed in terms of alcohol production by both its parent strain and the 227 Ng strain.

However, when mutant strain 13 was co-immobilized in accordance with the present invention with amyloglucosidase in cross-linked gelatin and the particles loaded into the column of a continuous fermenter, the ethanol level in the product stream reached 11% to 12% v/v in the steady state, that is to say, it gave an improved performance to parent strain CBS 252.86 in that it maintained this high level of alcohol continuously for up to 6 months and, additionally, reached its equilibrium level of alcohol production more quickly.

The major use of the biocatalysts of the present invention is in the conversion of carbohydrates but, depending upon the nature of the living cells, the biocatalysts will also find application in other microbiological processes of which the immobilized cells are capable.

According to a further aspect of the invention a substrate for alcohol production can suitably be pretreated with immobilized yeast/amyloglucosidase before passing substrate to a fermentor containing soluble yeast and amyloglucosidase.

According to still another aspect, the immobilized yeast biocatalyst according to the invention can be used for finishing a partially converted substrate for alcohol production. For example, a fermentable substrate containing 20% dry solids is converted in a first reactor to 9% ethanol (v/v) with soluble yeast and amyloglucosidase. This solution is fed into an immobilized yeast-/amyloglucosidase reactor according to the invention containing an alcohol resistant yeast, for example one of the yeasts belonging to the group described hereinbefore.

One major application of the biocatalysts where the living cells are yeast cells is the production of ethanol by fermentation of a fermentable sugar, especially under continuous fermentation conditions. As indicated above, the biocatalyst of the present invention has been found to be a particularly advantageous way of presenting yeast cells in a continuous fermenter where the biocatalyst is present in a fixed bed, a fluidized bed or a (continuously) stirred tank reactor (CSTR).

In a preferred embodiment of the invention the biocatalyst is present in a fluidized-bed reactor, wherein the reaction mixture is introduced in such a way that a uniform fluidization is achieved in the reactor. Advantageously, a multifunctional separation compartment is placed on the top of the reactor space for complete separation of the gas-liquid-solids mixture leaving the reaction space and for complete return of the biocatalyst into the reaction space. Such a fluidized-bed reactor with a multifunctional separation compartment has been described in EP-A 0,090,450 for the purification of waste water with biomass attached to carrier particles. It has now been surprisingly found that the same type of reactor can also be advantageously used for the preparation of ethanol, especially when using a biocatayst according to the present invention. The principle of the reactor with respect to the residence time vs. growth rate of the living cells such as yeast cells is similar to that disclosed in said European patent application and the specific conditions for optimal use can be easily determined by skilled persons, depending inter alia on the specific cells used.

The reactors are fed continuously with a feed stock of fermentable sugar and a product stream comprising ethanol is continuously removed. It is of course necessary to match the yeast and the fermantable sugar of the feedstock and, in accordance with one particularly advantageous embodiment, the biocatalyst may comprise our deposited strains of S. cerevisiae CBS 252.86 or CBS 253.86 together with amyloglucosidase and the feed stock may comprise dextrin. The dextrin may be a dextrin prepared by the enzymatic degradation of starch e.g. with α-amylase to give a dextrin of average degree of polymerization about 7–10 and the final degradation of the dextrins to provide a glucose feed stock achieved in the biocatalyst itself by the amyloglucosidase.

In the following Examples there are described several preferred embodiments to illustrate the invention. However, it should be understood that the invention is not intended to be limited to the specific embodiments.

EXAMPLE 1

40 g of dried instant yeat (*Saccharomyces cerevisiae* 2103 Ng, CBS No. 6131, 96.5% dry solid) were suspended in 960 ml of an aqueous solution containing 60 grams of gelatin at a temperature of about 40° C. The pH was adjusted to 5.5. This aqueous yeast-gelatin suspension was added with stirring to 4000 ml of n-butyl acetate which was previously heated to 40° C. The resulting suspension was rapidly cooled to 10° C. whereby yeast-gelatin-containing particles were formed. The n-butyl acetate was decanted. The particles (1 kg wet beads) were cross-linked with a solution of 30 g of glutaric dialdehyde (50% v/v solution) in 2000 ml of water adjusted to pH 6.5 for 1 hour at a temperature of 5° C. The particles were washed with water until the odor of n-butyl acetate could no longer be detected. The resulting particles had good physical stability and were insoluble in water. The entrapped yeast cells were batchwise incubated overnight in 3000 ml of the feed medium under aerobic conditions. The pH was kept at 4.5 with 0.1N NaOH and the temperature maintained at 35° C. by circulating water from a thermostatically controlled water bath, in the jacket.

The selected yeast culture was grown in a medium consisting of (% w/v): 22% glucose, 2% $NH_4Cl$, 0.5% $KH_2PO_4$, 0.1% NaCl, 1% $MgSO_4.7H_2O$, 0.2% $CaCl_2.2H_2$, Tween 80 (1 ml/l), Ergosterol (6.5 ml/l), 0.1% yeast extract, Vitamin B (7.5 mg/l) and antifoam (0.5 ml/l).

The amount of viable cells (plate counting on malt extract agar) encapsulated in the particles at the subsequent steps of the immobilization procedure are summarized in Table 1. No deteriorating effect of n-butyl acetate on the gelatinembedded yeast cells could be measured.

TABLE 1

| step in procedure | amount of viable cells/g dry mass beads | cells (%) |
| --- | --- | --- |
| yeast-gelatin suspension | $4 \times 10^9$ | 100 |
| after butyl acetate | $4 \times 10^9$ | 100 |
| after cross-linking | $5 \times 10^8$ | 40 |
| after regeneration | $6 \times 10^9$ | 150 |

EXAMPLE 2

In the same way as described in Example 1 but now starting with 40 g of dried instant yeast (*Saccharomyces cerevisiae* 2031 Ng, CBS No. 6128, 96.5% dry solid) and 8 ml of amyloglucosidase (AMIGASE LX, 26,000 AGI units/ml, Gist-Brocades) instead of the yeast only, cross-linked yeast-amyloglucosidase-gelatin particles were obtained, which were insoluble in water and had good physical stability.

EXAMPLE 3

Yeast-gelatin particles were prepared by the method described in Example 1 with the difference that *Saccharomyces cerevisiae* 1777 Ng, CBS No. 4877, 96.5% dry solid, was used and the particles obtained after the decantation of n-butyl acetate were cross-linked with glutaricdialdehyde in the presence of solubilized amyloglucosidase.

A solution of 30 g of glutaric dialdehyde (50% v/v solution) and 200 ml of amyloglucosidase (Amigase, of Example 2) in 200 ml of water and 1000 grams of wet beads were cross-linked for one hour at pH 6.5 and a temperature of 5° C.

After removal of the liquid, the amyloglucosidase-coated yeast-gelatin particles were washed several times until the cross-linking agent was entirely removed. The ethanol fermentation was carried out as described in Example 20. The amyloglucosidase-yeast-gelatin particles showed still higher operational stability as compared with the particles made according to the method of Example 2.

EXAMPLE 4

For the continuous production of the insolubilized microorganisms, the process was modified in the following way. The microorganism containing gelatin solution was pumped through a number of narrow tubes into a column containing n-butyl acetate which was kept at 5° C. The tubes, which were placed with their lower ends below the level of the butyl acetate, delivered a constant stream of the microorganism-gelatin solution which stream broke up into small droplets upon reaching the n-butyl acetate. The size of the droplets was dependent on the speed of the pump. The n-butyl acetate contained glutaric dialdehyde. The length of the column was 5 m so that the droplets which came down had ample time to gell and to react with the cross-linking agent. The beads obtained were continuously collected from the bottom of the column, separated from the n-butyl acetate and washed with water. The n-butyl acetate was recycled to the column after replenishment of the consumed glutaric dialdehyde. The column had an internal diameter of about 4 cm and produced about 8 l of the insolubilized microorganism beads per hour.

EXAMPLE 5

Co-immobilized microorganism-enzyme particles were continuously produced in the way as described in Example 4 but with the difference that a gelatin solution containing the enzyme(s) and microorganism(s) was extruded into the cold n-butyl acetate solution.

EXAMPLE 6

In a series of experiments, yeast-gelatin particles were prepared as described in Example 1 with the difference that the following organic solvents were used successively instead of n-butyl acetate:
toluene
petrol
petroleum ether (high boiling fraction, 70/110)
cyclohexane
n-pentane
In all cases the amount of viable cells after at least 1 hour of incubation in these organic solvents was 100%.

EXAMPLE 7

In the same way as described in Example 4 but replacing the yeast by *Acetobacter pasteurianum* strain ATCC 9325, insolubilized particles were obtained.

The amount of viable cells (plate counting on B.H.I. agar from Difco, pH 7.4) encapsulated in the particles at the subsequent steps of the immobilization procedure are summarized in Table 2. No deteriorating effect of n-butyl acetate on the gelatin-embedded Acetobacter cells and, also, no damaging of cells by glutaric dialdehyde was detected.

TABLE 2

| step in procedure | amount of viable cells % |
|---|---|
| Acetobacter-gelatin suspension | 100 |
| after butyl acetate extrusion | 100 |
| after cross-linking | 100 |

EXAMPLE 8

20 g of crab shell chitosan were dissolved in 450 ml of diluted acetic acid at 40° C. and neutralized to pH 6.0 with 30 g of sodium acetate. Then 250 g of wet cells of *Acetobacter pasteurianum* were suspended in the chitosan solution and the temperature kept on 40° C. Separately, 20 g of agar were dissolved in 500 ml of tap water and the temperature was increased to 100° C.

The agar solution was cooled to 45° C. and added to the Acetobacter-chitosan suspension. The suspension was extruded into n-butyl acetate at 5° C. as described in Example 4. The particles obtained were washed with water and cross-linked with glutaric dialdehyde, as described in Example 3, with the exception that the concentration of the cross-linking agent was twice as high.

The particles were insoluble in water and showed good physical stability.

EXAMPLE 9

250 g of a bacterial slurry (*Lactobacillus plantarus*, 3.5% dry solid) were suspended in 750 ml of an aqueous solution containing 60 grams of gelatin at a temperature of about 40° C.

This aqueous bacteria-gelatin suspension was added with stirring to 4000 ml of n-butyl acetate which was previously heated to 40° C. The resulting suspension was rapidly cooled to 10° C. and bacteria-gelatin-containing particles were formed. The n-butyl acetate was decanted. The particles (1 kg wet beads) were cross-linked with a solution of 30 g of glutaric dialdehyde (50% v/v solution) in 2000 ml of water adjusted to pH 6.5 for 1 hour at a temperature of 5° C. The particles were washed with water until the odor of n-butyl acetate could no longer be detected. The resulting particles had good physical stability and were insoluble in water. The entrapped bacterial cells were batchwise incubated in 3000 ml of the feed medium under microaerofiel conditions. The pH was kept at 6.0 with 10N NaOH and the temperature maintained at 30° C. by circulating water from a thermostatically controlled water bath, in the jacket. The selected bacterial culture was grown in a medium consisting of: 10 g/l pepton, 8 g/l Lab-Lemco, 4 g/l yeast extract, 20 g/l glucose, 1 g/l Tween 80, 2 g/l $K_2HPO_4$, 3 g/l sodium acetate, 2 g/l triammonium citrate, 0.2 g/l $MgSO_4.7H_2O$, 0.038 g/l $MnSO_4.H_2O$ and 60 g/l GISTEX.

The amount of viable cells (plate counting on MRS AGAR (OXOID CM 359) encapsulated in the particles at the subsequent steps of the immobilization procedure are summarized in Table 3. No deteriorating effect of n-butyl acetate on the gelatin-embedded bacterial cells could be measured.

TABLE 3

| step in procedure | amount of viable bacterial cell (%) |
|---|---|
| bacteria-gelatin suspension | 100 |
| after butyl acetate | 100 |
| after cross-linking | 1 |
| after regeneration | 10* |

(*9 × $10^8$ bacteria cells/g dry mass beads).

EXAMPLE 10

An actively growing culture of *Clostridium acetobutylicum* ATCC 824 (Weizmann strain) was inoculated (0.5%) into the medium described in Table 4 and incubated without pH control at 37° C. under nitrogen atmosphere. After 2 weeks, the contents of the fermentor were harvested and the spores washed twice with sterile demineralized water. A typical yield was 0.43 g spores (wet weight)/l glucose. One mg spores is equivalent to 2.3 × $10^{10}$ spores. The maximum growth rate ($\mu$max) of the culture under the conditions chosen was 0.36 $h^{-1}$. The washed spores were resuspended to a final concentration of 15 g/l (about 5 g/l dry weight) and aliquots were incubated for 1 hour at $\leq 5°$ C. in the presence of glutardialdehyde (up to 1% w/w). After washing with sterile demineralized water, a dilution series inoculated into brain-heart infusion containing glucose (10 g/l) was heat shocked (2 min. at 80° C.) and incubated at 37° C. No effect of glutardialdehyde on spore viability was observed. Spores were immobilized (0.2% w/w) in gelatin (6.0% w/w) cross-linked with glutardialdehyde (0.75% w/w) according to the standard procedure for yeast/amyloglucosidase. Spore viability was checked at intervals during the treatment. After hydrolysis of the gelatin by a proteolytic enzyme suspension, a dilution series was plated on BHI agar containing glucose (10 g/l) and dithiothreotol (0.08% w/w) after heat activation of the spores. The counts obtained after incubation at 37° C. for 1 week in anaerobic jars showed that the viability of *C. acetobutylicum* spores is not affected by the immobilization procedure used.

TABLE 4

| MEDIUM COMPOSITION (per liter destilled water) | |
|---|---|
| K-phosphate buffer | 15 mM |
| $MgSO_4.6H_2O$ | 0.2 g |
| $NH_4Cl$ | 0.65 g |
| yeast extract | 5.0 g |
| tryptone | 5.0 g |
| vitamins sol[n] | 0.5 ml |
| trace elements sol[n] | 9.0 ml |
| resazurin (0.1%) | 1.0 ml |
| $Na_2S$-cysteine HCl (5%) | 10.0 ml |
| glucose | 30.0 g |

| Vitamins: | | Trace elements: | |
|---|---|---|---|
| Biotin | 40 mg/l | nitrilotriacetic acid | 12.8 g/l |
| pABA | 100 mg/l | $FeSO_4.7H_2O$ | 0.1 g/l |
| Folic acid | 40 mg/l | $MnCl_2.4H_2O$ | 0.1 g/l |
| Ca pantothenate | 100 mg/l | $COCl_2.6H_2O$ | 0.17 g/l |
| nicotinic acid | 100 mg/l | $CaCl_2.2H_2O$ | 0.1 g/l |
| vitamin B12 | 2 mg/l | $ZnCl_2$ | 0.1 g/l |
| thiamine.HCl | 10 mg/l | $CuCl_2$ | 0.02 g/l |
| pyridoxine.HCl | 100 mg/l | $H_3BO_3$ | 0.01 g/l |
| thioctic acid | 100 mg/l | $NaMoO_4.2H_2O$ | 0.01 g/l |
| riboflavin | 10 mg/l | NaCl | 1.0 g/l |
| | | $Na_2SeO_3$ | 0.02 g/l |
| | | $NiCl_2$ | 0.1 g/l |

EXAMPLE 11

*Lactobacillus plantarus* was immobilized as described in Example 9 but a mixture of gelatin (6% w/w) and chitosan (Sigma, C-3646), 0.5% w/w was used to immobilize the Lactobacillus cells. The amount of viable cells (plate counting as described in Example 9) encapsulated in the particles at the subsequent steps of the immobilization procedure are summarized in Table 5.

TABLE 5

| Step in procedure | Amount of viable cells % |
|---|---|
| Lb11-gelatin-chitosan suspension | 100 |
| after butyl-acetate | 100 |
| after cross-linking | 1* |
| after regeneration | >10 |

*1% = 2 × $10^6$ cells/g dry mass beads.

EXAMPLE 12

The procedure described in Example 11 was repeated but now a mixture was used of gelatin (6% w/w) and polyethylenimine (sp-200 Nippon Shokubai), 2% w/w to immobilize yeast cells. The amount of viable cells (plate counting as described in Example 1) encapsulated in the particles at the subsequent steps of the immobilization procedure are summarized in Table 6.

TABLE 6

| step in procedure | amount of viable cells % |
|---|---|
| yeast-gelatine-PEI suspension | 100 |
| after butyl-acetate | 100 |
| after crosslinking | 1* |
| after regeneration | 150 |

*1 × $10^4$ cells/g dry mass beads.

EXAMPLE 13

The procedure described in Example 9 was repeated but now a mixture was used of gelatin (4% w/w) and an alginate amine (2% w/w). Said alginate amine derivative was prepared as follows: to a solution of 20 g of Manucol E/RE pH 3.5 in 750 ml of distilled water was added quickly but in small portions to a solution of 23 g (0.2 mol) of 1,6-hexanediamine in 200 ml of distilled water, of which the pH was adjusted to 10.0 by addition of concentrated acetic acid. The reaction mixture was stirred for 4 hours at room temperature and then diluted with 1.0 l of methanol. The precipiate was filtered and washed twice with 200 ml of methanol. After drying in vacuo at 50° C., a white powder was obtained which appeared to be a useful support material for enzymes and microorganisms. After cross-linking with glutardialdehyde (see Example 1), insoluble particles were obtained which had good physical stability and viable cells counts comparable with data as given in Table 6.

EXAMPLE 14

75 g of a slurry of plant cells (*Tagetes minuta*; 1.5% w/w dry mass) were suspended in 175 ml of an aqueous solution containing 17 g of gelatin at a temperature of about 40° C. and a pH of 5.0. The plant cells containing gelatin solution were pumped through a number of narrow tubes into a column containing n-butyl acetate which was kept at 5° C. The tubes which were placed with their lower ends below the level of the butyl acetate, delivered a constant stream of the plant cells-gelatin solution which stream broke up into small droplets upon reaching the n-butyl acetate. The size of the droplets was dependent on the speed of the pump. The length of the column was 5 m so that the droplets which came down had ample time to gell. The beads obtained were continuously collected from the bottom of the column, separated from the n-butyl acetate and washed with water. The n-butyl acetate was recycled to the column. The column had an internal diameter of about 4 cm and produced about 8 l of the insolubilized plant cell beads per hour. Then the particles were cross-linked with variable concentrations of glutaric dialdehyde at 5° C. and pH 6.0 for one hour. The particles obtained were washed extensively with tap water. They were insoluble in water and showed good mechanical stability.

EXAMPLE 15

The procedure described in Example 14 was repeated with petrol instead of n-butyl acetate. Also in this experiment, good mechanically stable and water-insoluble particles were obtained.

EXAMPLE 16

In a series of experiments, yeast-gelatin particles were prepared as described in Example 4, but now zirconium oxide powder (325 mesh) was added to the yeast-gelatin suspension before the extrusion into cold n-butyl acetate. It appeared that the higher the amount of $ZrO_2$ added, the higher the density of wet particles obtained. Results of a typical series of experiments are shown in FIG. 1.

EXAMPLE 17

A small amount of phosphatidylcholine (lecithine) was added to butyl acetate in the experiment described in Example 4. This resulted in the production of small fibers instead of small beads.

EXAMPLE 18

Fluidized-Bed Dewatering protocol 20 g of wet particles of co-immobilized amyloglucosidase and yeast were prepared as described in Example 2. In order to increase the storage stability, the yeastamyloglucosidase-gelatin particles were dried on a laboratory discontinuous fluidizer in 20 to 30 minutes, taking care that the temperature of the yeast granulate did not exceed 40° C. Great attention was paid to the fluidization with air and to the start of the drying process which was carried out quickly while the at the initial phase. The resulting particles contained 85 to 93% of dry matter. Neither the yeast cells nor the co-immobilized amyloglucosidase showed any loss of activity over a period of 12 months when stored in vacuo at 5° C.

EXAMPLE 19

The yeast-gelatin-containing particles obtained according to the method described in Example 1 were used in a bioreactor (CSTR) (working volume: 800 ml) by filling with 350 g of wet particles and passing a sterilized 20% (w/v) solution of glucose added to the growth medium described at pH 4.5 through the reactor at different flow rates. The temperature was kept at 32° C. The bioreactor was kept in operation continuously for four months. Samples for the determination of ethanol, glucose and glycerol were taken from the effluent over this period. No precautions were taken to maintain the sterility but no contamination was observed.

The results obtained demonstrate the high operational stability of the immobilized yeast cells at an average ethanol concentration of 8.0 to 8.5% by volume.

EXAMPLE 20

The yeast-amyloglucosidase-gelatin particles obtained according to the method described in Example 2 were regenerated and used in the same way as described in Example 19 but with a 20% (w/v) solution of maltodextrin with an initial DE value of 15 (Snowflake) instead of glucose.

Figure 2:
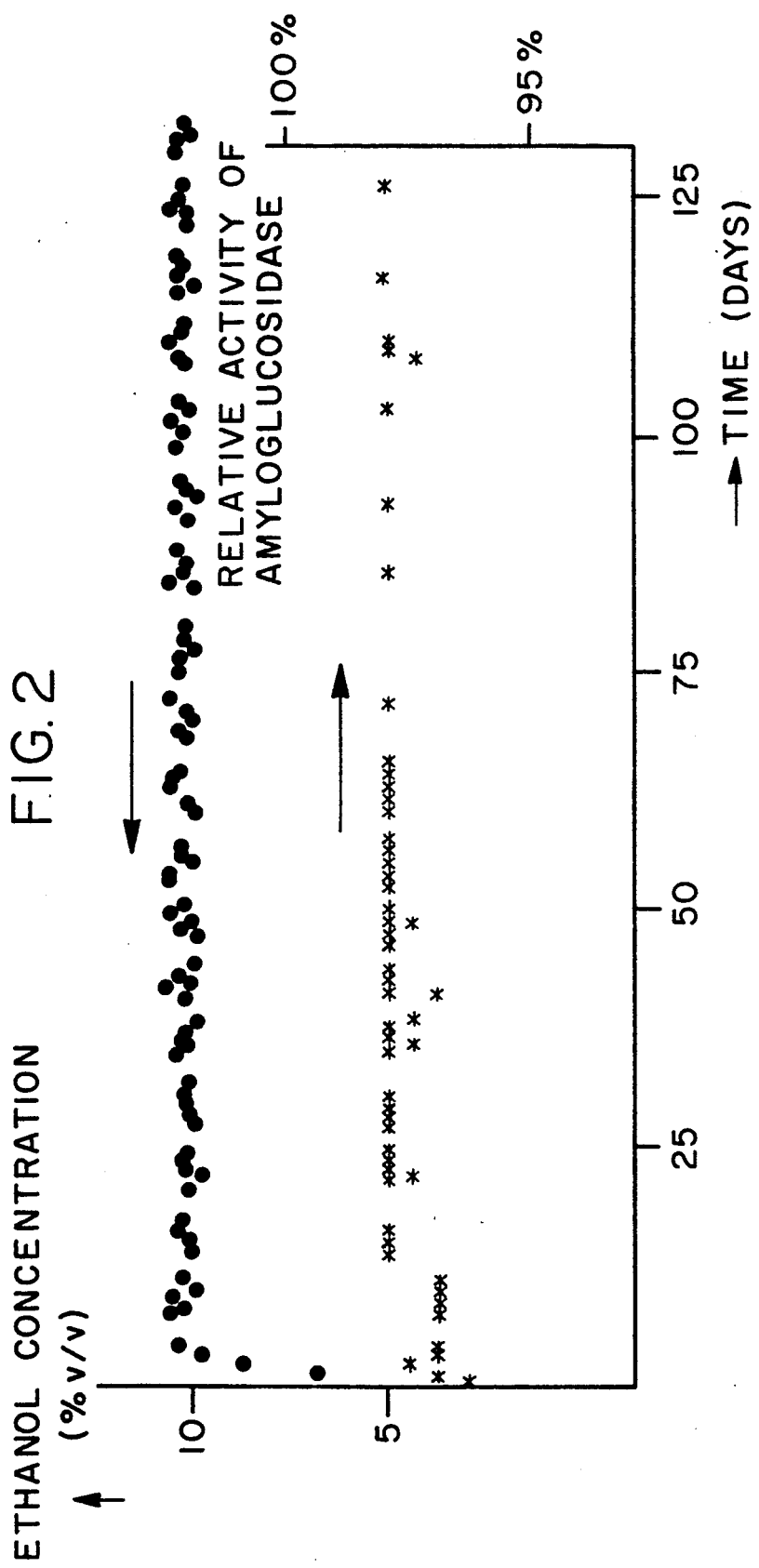

The results are shown in FIG. 2 and demonstrate the high operational stability of the co-immobilized amyloglucosidase and yeast cells used and the possibility to convert the DE-15 maltodextrin substrate into ethanol in a one-step operation. The average ethanol concentration was 8.5% by volume.

EXAMPLE 21

The Acetobacter-gelatin-containing beads obtained according to the method described in Example 7 were used in a bioreactor (CSTR) (working volume 800 ml) by filling with 80 g of wet beads and 720 ml of a sterilized medium with 5% (w/v) solution of glucose and 2% (w/v) solution of yeast extract. The medium was buffered with phosphate on pH 7.0. After 16 hours of incubation at a temperature of 30° C., samples were taken and analyzed for glucose and acetic acid.

The final concentration of acetic acid was 0.5 g/l and the rate of acid production was measured to be 21 mg of acetic acid per g of cells (dry mass) per hour.

The same experiment was also carried out with ethanol as the substrate instead of glucose. In the latter case, the final concentration of acetic acid was 0.8 g/l and the production rate was 31 mg of acetic acid per g of cells (dry mass) per hour.

EXAMPLE 22

The *Lactobacillus plantarus* cells-gelatin-containing particles obtained according to the method described in Example 9 were used in a bioreactor (CSTR) (working volume: 800 ml) by filling with 140 g of wet particles together with 300 ml of the medium described in Example 9.

Figure 3:
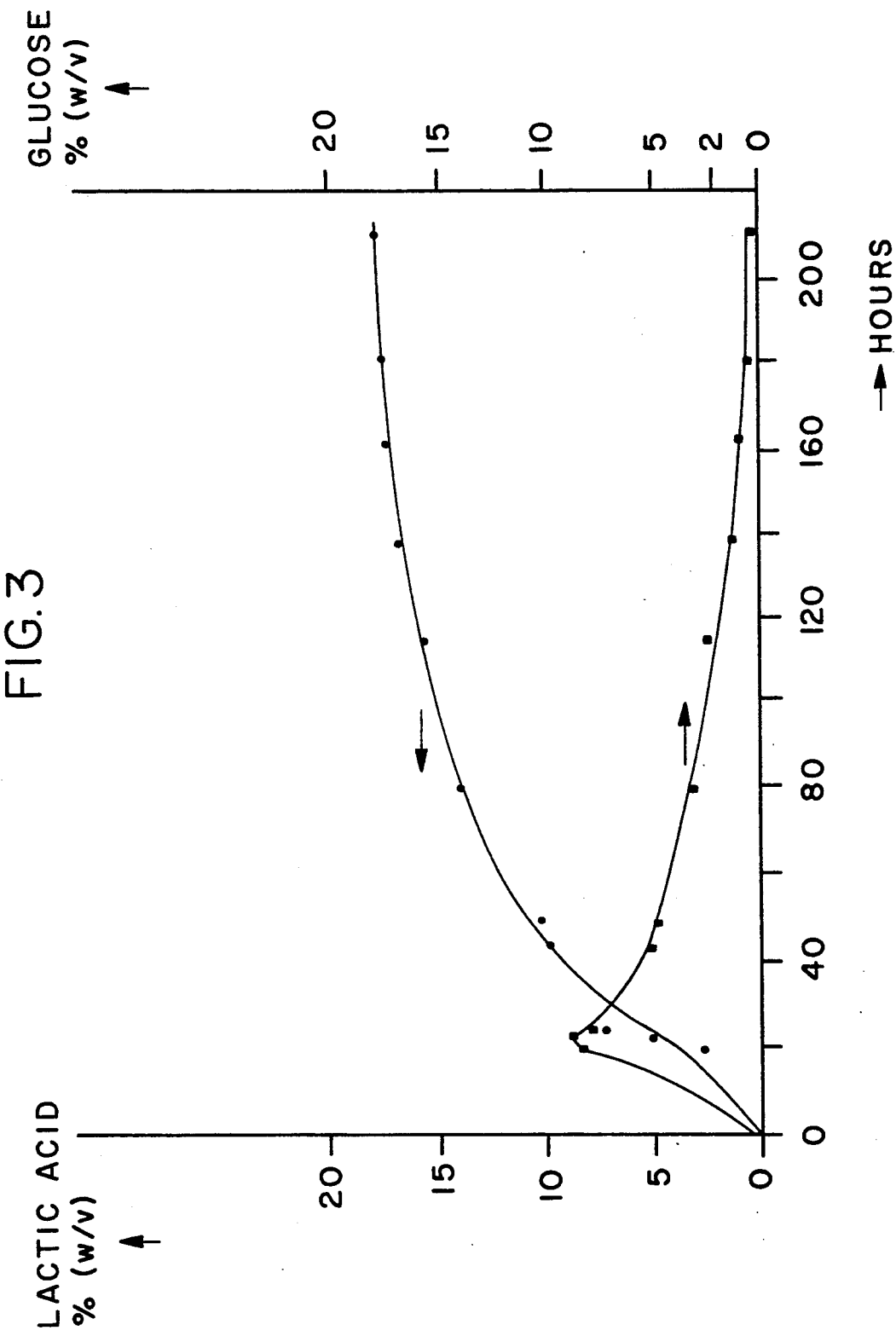

At the start of the fermentation, 352 ml of a 48% (w/w) glucose solution was added to the fermentor with a speed of 16 ml/hr during 22 hours. The temperature was kept at 30° C. and the pH was kept at 6.0 with 10N NaOH. The total batchwise fermentation time was six days and during this period, samples were taken for the determination of glucose and lactic acid. No precautions were taken to maintain the sterility but no contamination was observed. The results obtained demonstrate a high productivity of lactic acid and a remaining high yield up to 96% at the end. The lactic acid concentration at the end of the fermentation was 17.8% (w/v) as shown in FIG. 3.

EXAMPLE 23

Figure 4:
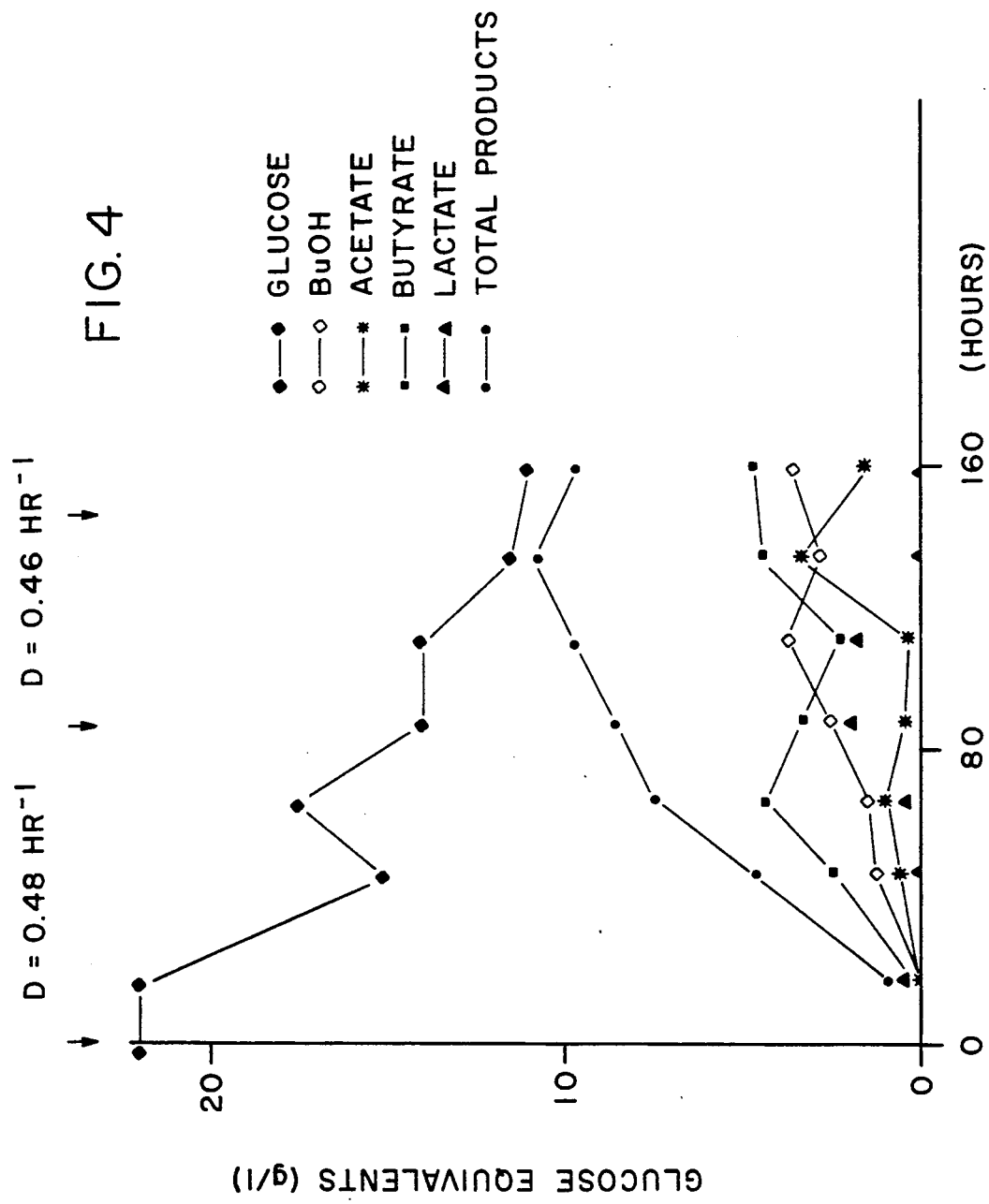

A CSTR (culture volume 0.51) gassed with $N_2$, and the medium described in Table 4, were used for the fermentation of organic solvents with immobilized Clostridium cells as described in Example 10. "Sterilization" of the beads (0.25 l containing 2 g/l spores) and activation of germination were achieved using aqueous ethanol (50% w/w) according to the method of Krouwel (Biotechnol. Letts. 3 (1981) page 158 to 159). The ethanol was removed by washing with sterile physiological salts before medium addition. Only the germination and growth phases were followed. The fermentation results obtained for the first 160 hours are shown in FIG. 4. Glucose was converted to butanol, butyrate, acetate and lactate. Traces of acetone were occasionally seen (not shown). The maximum butanol productivity obtained was 0.76 g/l h at a glucose conversion rate of 5 g/l h.

Scanning electron micrographs of the beads at various stages in the culture showed that the spores and some residual cells were evenly distributed through the gelatin matrix and that complete colonization of the beads was achieved in 7 days.

EXAMPLE 24

Figure 5:
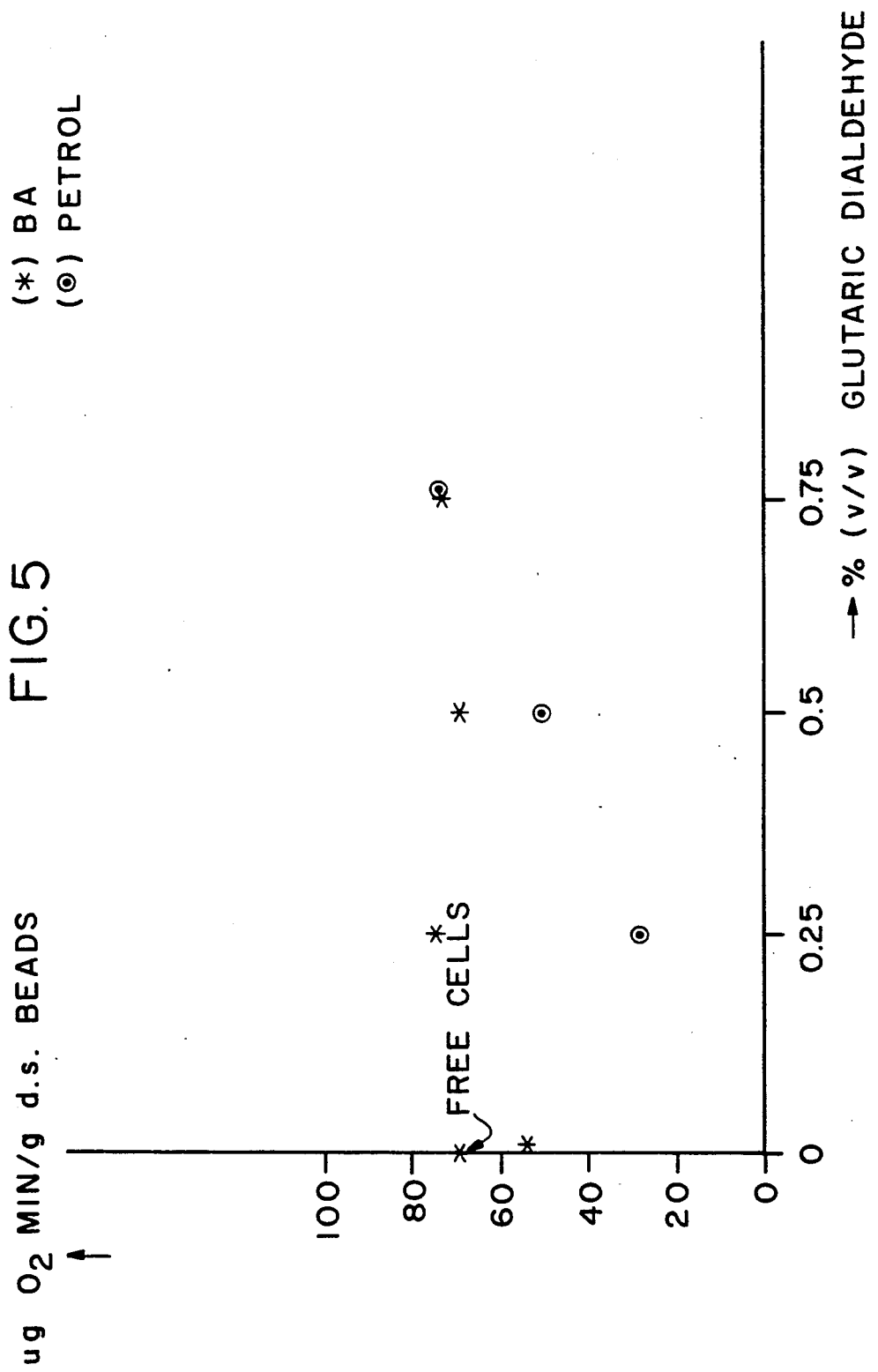

Oxygen consumption of the immobilized plant cells as described in Examples 14 and 15 was measured in Murashige and Skoog medium with 2% w/v sucrose. Results are shown in FIG. 5. Oxygen consumption of the immobilized *Tagetes minuta* cells was in the same order of magnitude as cells in suspension.

EXAMPLE 25

Mutation of *S. cerevisae* IFO 0203 (CBS 252.86)

The method was based on the continuous culture of yeast, employing growth dependent pH changes to control the rate of addition of fresh medium to the fermenter (the "phauxostat"). The method has been described by G. A. Martin and W. P. Hempfling, Arch. Microbiol. 107 (1976) Pages 41 to 47. A 1L Gallenkamp fermenter was filled with the basic minimal medium, having a composition as set out below. An alcohol level of 3% v/v was established initially. All operations were carried out under sterile conditions and the fermenter, containing 0.5 l of his complex medium was seeded with a pre-grown culture of *S. cerevisiae* IFO 0203 (CBS 252.86). The pH was initially maintained at 4.5, the fermenter being provided with an inlet for N NaOH which was injected when necessary to maintain the pH at 4.5. The fermenter had also an inlet for fresh medium, controlled by the 'phauxostat' so that the glucose concentration was never limiting. The initial temperature setting was 32° C. When the fermenter reached steady state operation, the temperature was increased to 40° C. The fermenter was run continuously for seven months.

In accordance with the protocol set out below, the yeast mass was pulsed with mutagens when the alcohol concentration became limiting and, on each subsequent occasion when alcohol concentration again became limiting, the yeast mass was again pulsed with mutagens. Initially, ethyl methanesulfonate (EMS) was injected in an amount such that, immediately after injection, the concentration of EMS in the fermenter was at the percentage w/v indicated below. After three injections of EMS, subsequent injections were with an aqueous solution of sodium nitrite in amounts such that, immediately after injection, the concentration of sodium nitrite in the fermenter was in millmoles per liter as indicated below.

The concentration of the basic medium was as follows:

|  | g/l |
|---|---|
| $NH_4Cl$ | 2.5 |
| $KH_2PO_4$ | 0.25 |
| $MgSO_4.7H_2O$ | 0.1 |
| NaCl | 0.05 |
| Spore Elements | 0.1 (ml) |
| Vitamins | 0.5 (ml) |
| Ergosterol | 1.72 (mg) |
| Tween 80 | 0.25 |
| Glucose | 100 g |

The mutagen pulsation protocol was as follows:

| Time after seeding (hours) | mutagen pulse |
|---|---|
| 160 | 0.01 EMS |
| 460 | 0.1 EMS |
| 650 | 1.0 EMS |
| 1200 | 0.1 mM $NaNO_2$ |
| 1430 | 0.5 mM $NaNO_2$ |
| 1600 | 1.0 mM $NaNO_2$ |
| 1820 | 2.0 mM $NaNO_2$ |
| 1960 | 3.0 mM $NaNO_2$ |

Samples were withdrawn at regular intervals and after a total of 2490 hours, a withdrawn sample was diluted and plated on malt agar containing 6% ethanol. 16 good growing colonies were further analyzed in the 6 hours 37° C. alcohol production test as described previously when it was found that the various mutant strains isolated gave rise to ethanol concentrations between 2.53 and 3.61% v/v after 6 hours cultivation at 37° C. The colony that gave rise to the 3.61% value was designated mutant 2490 KI13 and was the mutant deposited as CBS 253.86 as described above.

Fermentation of the main culture was continued and a further sample taken after a total of 4860 hours cultivation.

The various samples isolated were again tested for alcohol production in 6 hours at 37° C. by the procedure previously described when it was found that the mutants obtained could produce somewhere between 2.69 and 3.56% v/v ethanol. The sample producing 3.56% ethanol was designated mutant 4860KI1 and the mutant producing 3.31% ethanol was designated mutant 4860 KI6.

EXAMPLE 26

Figure 6:
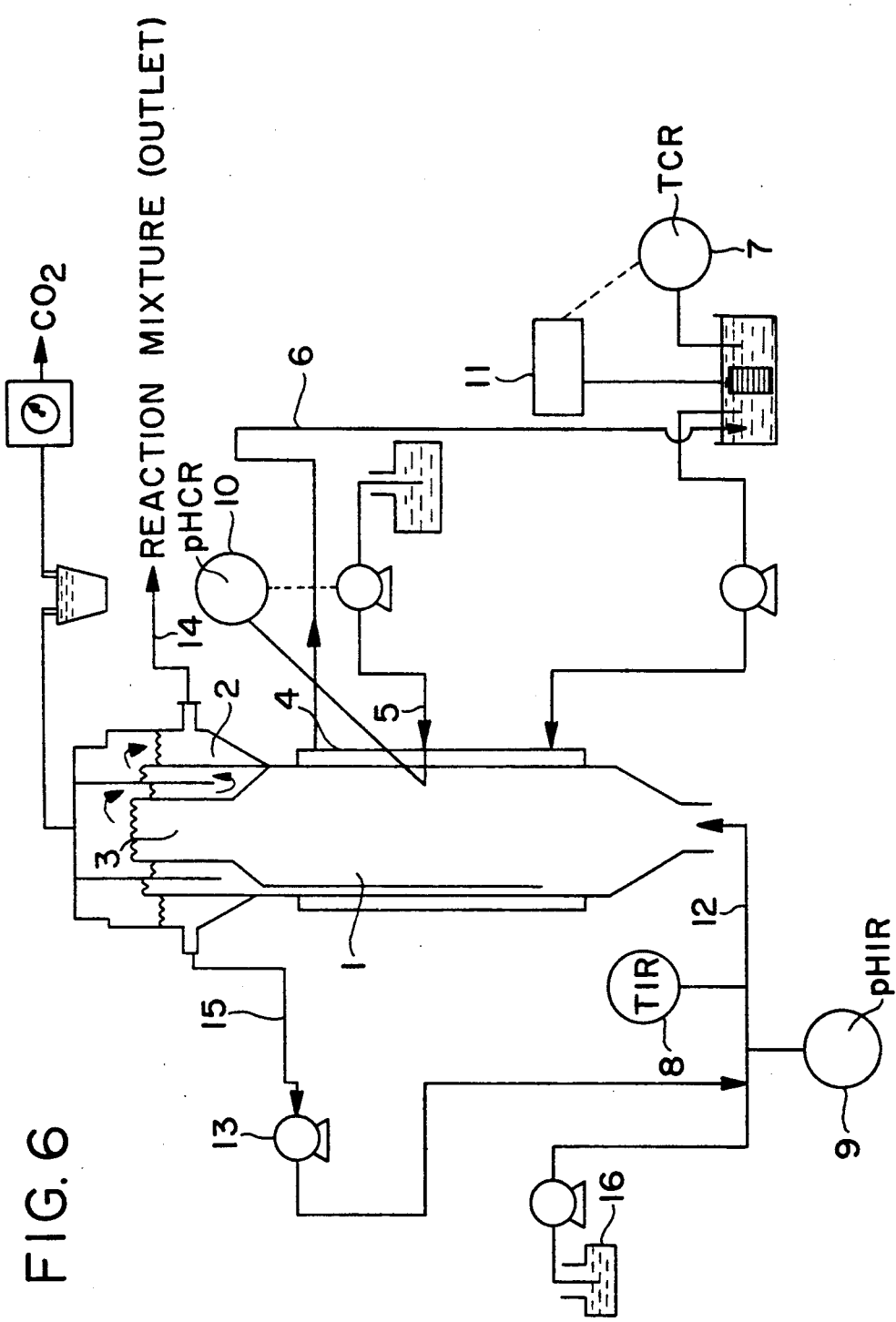

Fermentation was carried out in fluidized bed reactor of the type illustrated in FIG. 6.

The fermenter consists essentially of a fluidized bed. part (1) in the form of a column 6 cm inside diameter and 1500 cm high, topped with a settling compartment (2) of inside diameter 14 cm and a gas separating section (3) inside settler (2). The fluidized bed part (1) is fed from below by feedstock pipe (12) and settling compartment (2) is provided with an outlet port (14) and a recycling port (15). The fluidized bed part (1) is thermostatically controlled by a water jacket (4). Water jacket (4) is fed via line (6) and controlled by temperature controlling device (7) and cooling water reservoir (11). The pH inside the fluidized bed part (1) is controlled by a pH controlling device (10) which controls a feed of alkali through injection pipe (5). Feedstock is supplied to the fluidized bed part (1) through inlet (12) from feedstock storage (16), inlet (12) being provided with a temperature indicating device (8) and pH indicating device (9). Recycle substrate leaving settling compartment (2) via line (15) is recycled through pump (13) back through inlet (12).

A substrate of the following composition was prepared.

| A. Maltodextrins (DE 8-10) | 160 g/l |
|---|---|
| $NH_4Cl$ | 2.5 g/l |
| $KH_2PO_4$ | 0.25 g/l |
| B. Basal salts | |
| $CaCl_2.2H_2O$ | 2.0 g/l |
| $MgSO_4.7H_2O$ | 10.0 g/l |
| NaCl | 1.0 g/l |
| C. Spore-elements | |
| citric acid | 0.250 g/l |
| $FeSO_4 (NH_4)_2SO_4.6H_2O$ | 0.450 g/l |
| $ZnSO_4.7H_2O$ | 0.084 g/l |
| $CuSO_4.5H_2O$ | 0.013 g/l |
| $MnSO_4.4H_2O$ | 0.010 g/l |
| $H_3BO_3$ | 0.010 g/l |
| $Na_2MoO_4.2H_2O$ | 0.010 g/l |
| KI | 0.005 g/l |
| D. Vitamins | |
| Inositol | 0.200 g/l |
| Nicotine acid | 0.010 g/l |
| Ca-D-penthothenate | 0.010 g/l |
| Vit. B1 | 0.010 g/l |
| p-aminobenzoic acid | 0.006 g/l |
| Vit. B6 | 0.001 g/l |
| D-biotin | $0.04 \times 10^{-3}$ g/l |
| Ergosterol | 0.001 g/l |
| Tween-20 | 0.250 ml/l |
| Anti-foam | 0.25 ml/l |

The maltodextrin solution, the basal-salts medium, the vitamin solution and the spore-elements solution were sterilized for 20 minutes at 120° C. separately. After sterilization the four solutions were added together with a composition as described.

The fluidized bed reactor (FIG. 6) was filled up with beads (average diameter: 1.8 mm) for 50% (E=0.5) of the working volume (1). These beads consist of reactivated yeast cells and amyloglucosidase immobilized into a cross-linked gelatin support material as described in detail in Example 2. The experiments presented in this Example were carried out with the following types of yeast strains:
1. Saccharomyces cerevisiae (bakers' yeast, 227 Ng)
2. Saccharomyces cerevisiae CBS 252.86
3. Saccharomyces cerevisiae CBS 253.86

Maltodextrin (Morsweet, CPC) solution was continuously supplied to the fermentor from (11), at a specified rate so that all the oligosaccharides could be saccharified and converted in ethanol. The temperature was kept at 32° C. and the pH at 4.15 by adding 4.0N NaOH.

production of ethanol with an average ethanol concentration in the third stage of 10.4% by volume.

Table 7 summarises average specific reaction rates, ethanol concentrations, yields and production rates in the three stages.

TABLE 7

|  | Specific reaction rate (moles ethanol/kg (wet beads)/hr) | Ethanol concentration | Yield (%) | Production rate (moles ethanol/hr) |
| --- | --- | --- | --- | --- |
| Stage 1 | 0.85 | 5.2 | 94 | 0.170 |
| Stage 2 | 0.50 | 8.2 | 94 | 0.099 |
| Stage 3 | 0.22 | 10.4 | 93 | 0.072 |

The substrate was continuously fermented under the above conditions. To assist the beads in fluidization, the linear velocity of the reaction mixture was adjusted to 0.15 cm/sec by pump (13) on the circulating pipe (12). The ethanol concentration of the effluent mixture, the concentration of sugars as maltodextrins, maltose and glucose, and the glycerol concentration were measured every day by using a High Pressure Liquid Chromatograph with a carbohydrate column type HPX 07C Bio-Rad..

Figure 7:
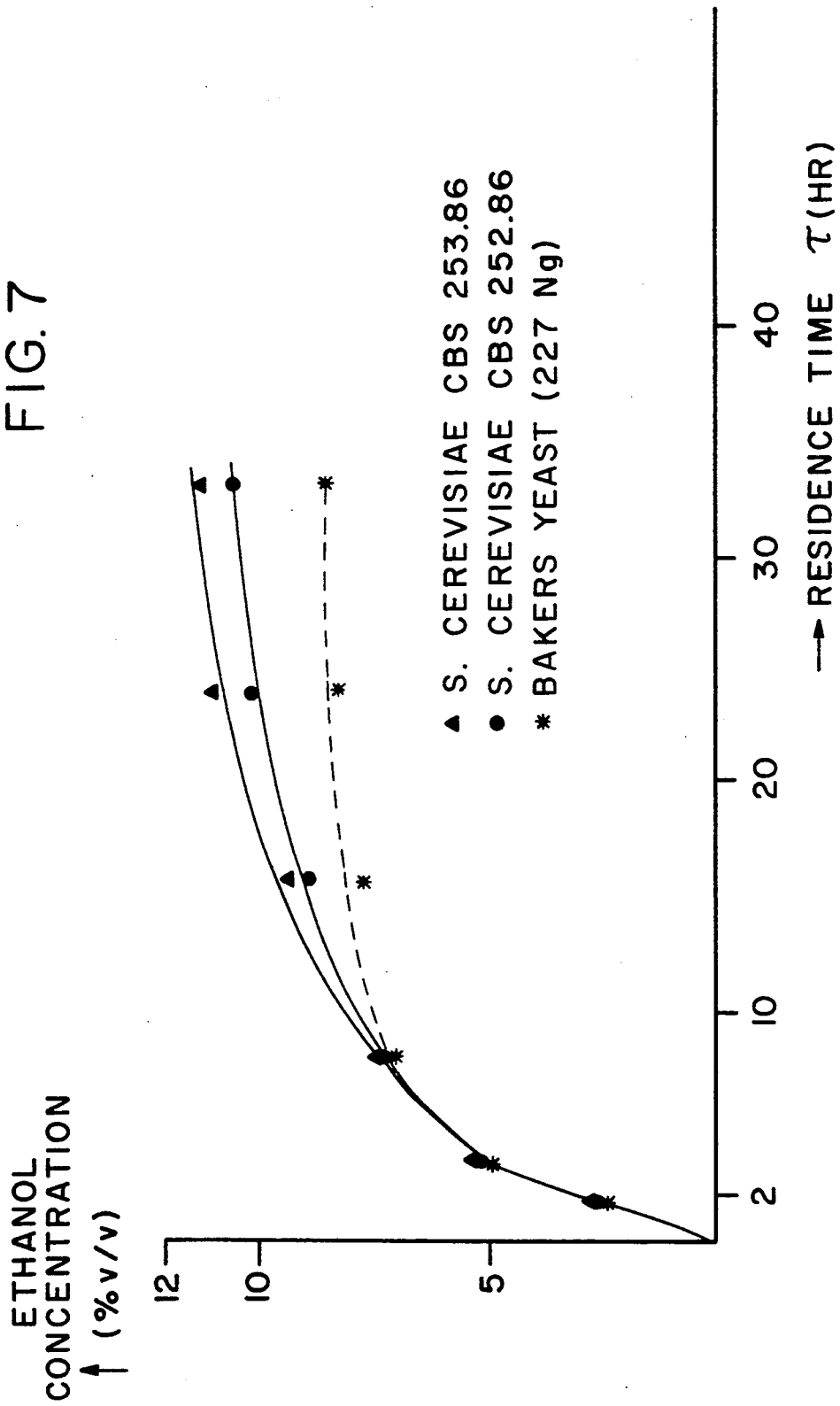

FIG. 7 shows the relationship and the dilution rate of the substrate in the reactor and the final ethanol concentration with the 3 different types of yeast strains used. Every steady state was kept for one week. Surprisingly only the yeast strains CBS 252.86 and CBS 253.86 could reach a final ethanol concentration of more than 10.5% of volume and a glycerol concentration of less than 2% compared with a final ethanol concentration of less than 9% for the bakers' yeasts and a glycerol concentration of more than 3% v/v. Additionally the equilibrium level of alcohol production was reached earlier with CBS 253.86.

EXAMPLE 27

Figure 8:
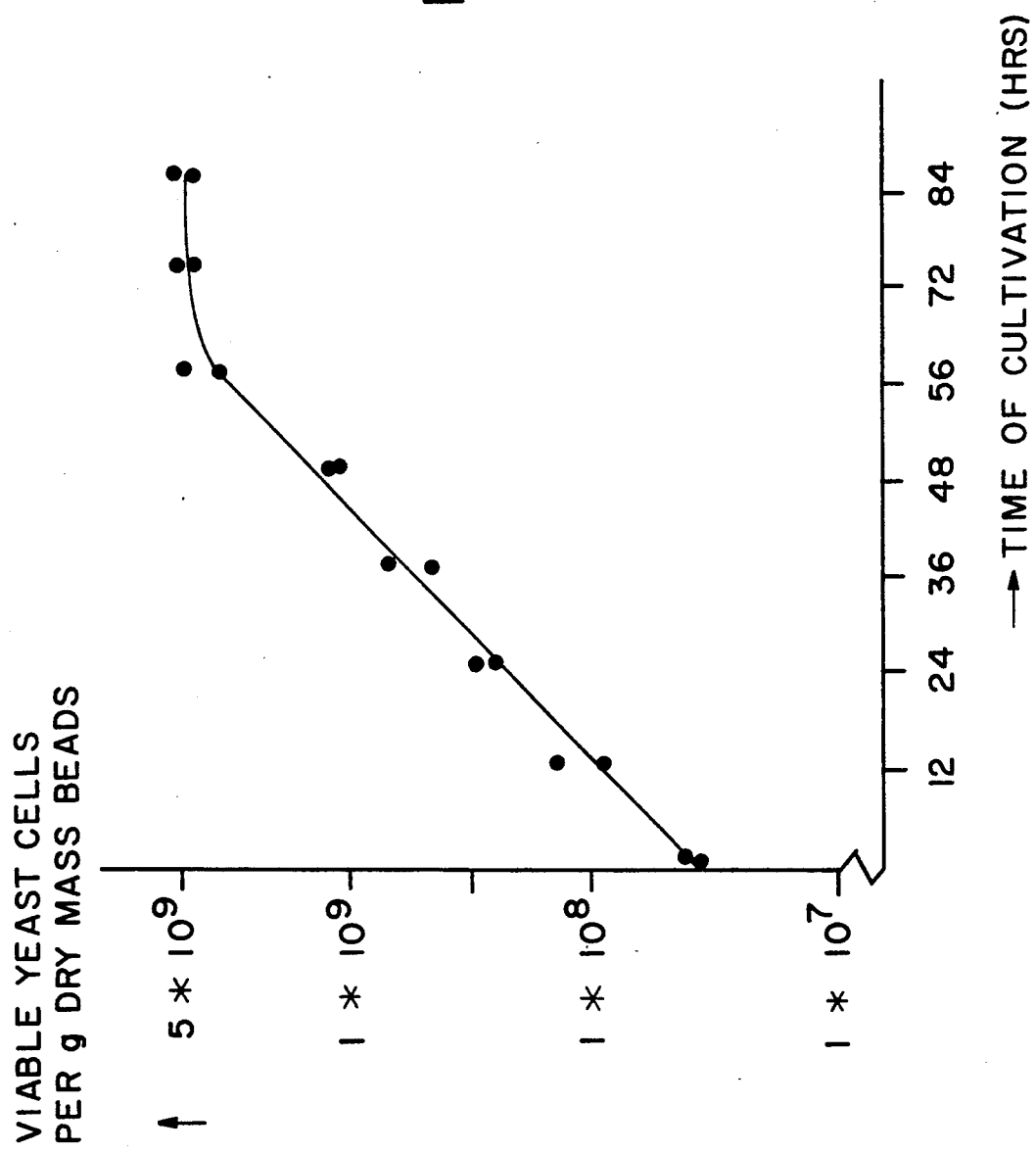

*Saccharomyces cerevisiae* CBS 253.86 was immobilized in gelatin as described in Example 1 and incubated with the fermentation medium of Example 1 in the presence of oxygen. The growth of yeast cells in the beads was measured in time by plate counting. FIG. 8 shows the average viable cells concentration per g dry mass beads in relationship with the time of cultivation.

A final concentration of at least $4 \times 10^9$ cells per g dry mass beads could be obtained. By loading the fluidized bed reactor of Example 26 with these activated beads, high concentrations of yeast cells per reactor volume were achieved. FIG. 9 shows the number of yeast cells per $m^3$ reactor versus the loading of the reactor with beads. The concentration of yeast cells was at least ten times the concentration obtained in non-immobilized reactor systems such as cell recycle reactors.

EXAMPLE 28

Highly activated beads with co-immobilized amyloglucosidase and *S. cerevisiae* CBS 253.86 (see Example 27) were used in a fermentation system of three fluidized bed reactors as described in Example 26 but connected in series with each other. Each reactor was filled with beads up to 40% w/v of the working volume.

The volumes of the first stage, the second stage and the third stage were respectively, $V_1=500$ ml; $V_2=480$ ml and $V_3=800$ ml. The residence times (T) of the food in these reactors were $T_1=2.63$ h; $T_2=2.53$ h and $T_3=4.21$ h. Results of final ethanol concentration and residual activity of amyloglucosidase are given in FIG. 2. This figure shows a stable reactor system for the

EXAMPLE 29

Acetone Dewatering Protocol

Cross-linked beads are placed in approximately four volumes of 20% acetone. The solution and beads are stirred and the beads are allowed to contact the solution for 20 minutes. The 20% acetone solution is decanted and four volumes of 40% acetone are added. This solution and beads are stirred and the 40% acetone solution is decanted after 20 minutes. This procedure is repeated with 60%, 80% and 100% acetone, respectively. After 20 minutes in 100% acetone, the acetone is decanted and an additional four volumes of 100% acetone is added and allowed to stand for an additional 30 minutes. The beads may then be rinsed with several volumes of tap water to remove the surface acetone.

EXAMPLE 30

Fluidized-bed Dewatering Protocol

Cross-linked beads (74 kg—approximately 10% dry matter) are placed in a conical fluidized-bed drier. The initial bed temperature was 20° C. with a flow rate of air of 2300 kg/hr (±2.1 m/sec). After 140 minutes, the beads become free-flowing and the bed temperature was raised to 30° C. The overall time of drying was 3 hours. The dried beads have a dry matter content of 82 to 84%.

EXAMPLE 31

Selection of Ethanol Tolerant Yeast Strain for High Ethanol Production in an Immobilized Biocatalyst System Six potential ethanol tolerant yeast strains were initially screened for ethanol tolerance by plating on YM Medium supplemented with ethanol at concentrations of 12, 15 and 18% (v/v).

The first strain chosen for selection based on consistent positive growth on 18% ethanol was ETS5, a Red Star Cantarelli Champagne variety of *Saccharomyces bayanus*.

Four cultures of ETS5 were recovered from 18% ethanol plates and transferred to YM Broth. When enough growth was achieved, aliquots of yeast from each of the four cultures were used to inoculate glucose containing media for fermentation.

Of the four cultures, ETS5S2 performed best at 16.4% (v/v) ethanol in 54 hours. This cultures was chosen to undergo mutation to enhance ethanol production.

YM Broth supplemented with 18 and 21% (v/v) ethanol was inoculated with ETS5S2. The flasks were left for 72 hours, treated with sodium nitrite (0.1% w/w) and 72 hours later plated on YM supplemented with ethanol and incubated for 24 hours.

After incubation, six cultures, designated ETS5Ml-6, were recovered. The six cultures were grown in YM for 48 hours. Each of the six cultures was used to inoculate a fermenter containing 7% (v/v) ethanol plus supplemental glucose since this strain does not exhibit enough osmotolerance to grow well at extremely high concentrations of glucose. Each fermenter was equipped with a pH controller connected to a glucose pump and level controllers to shut off the glucose pump as well as an outlet pump to maintain a consistent level in the fermenter. When approximately 2.5% ethanol was produced, the pH would drop sufficiently to activate the glucose pump and glucose was fed into fermenter until the level controller shut it off. After the yeast fermented glucose to 12.5% (v/v) ethanol, sodium nitrite (in 0.5% w/w increments) was added to the fermenter each time the glucose pump switched on.

The cultures were allowed to ferment for 96 hours. After fermentation ETS5Ml yielded 21% (v/v) ethanol and was thus chosen for immobilization.

EXAMPLE 32

114 grams of deionized water was heated to 58° C. 16 grams of gelatin were added to the water and stirred until dissolved, while the temperature was maintained at 50° to 58° C. The mixture was cooled to 45° C. The pH of the solution was 5.6 and was not adjusted. 50 grams of a 4% chitosan solution (in 4% acetic acid) was added to the mixture and stirred until well mixed.

Cells of the yeast strain *Saccharomyces bayanus* (23 to 25 grams) are resuspended in an appropriate amount of DI water to give a final weight of 50 grams. This mixture is added to the gelatin/chitosan mixture and stirred until cells are uniformly suspended. (The additional water is used to correct the viscosity of the mixture, so that it will flow dropwise through a 15 G needle). The final mixture is maintained at 45° C. in a waterbath.

Approximately 30 ml aliquots of mixture is transferred to a jacketed chromatography column (maintained at 45° C.) adapted with a 15 G needle through which the enzyme/organism/gelatin/chitosan mixture flows dropwise into a 900 ml volume of cold butyl acetate (7° C.). The droplets form beads which are stirred in the butyl acetate by a stir bar in the bottom of the 1000 ml tall-form beaker.

When ½ of the mixture volume is formed into beads, they are washed with approximately 8000 ml of ice water to remove the excess butyl acetate after the majority of the butyl acetate is decanted off the top of the beads.

400 ml of fresh ice water is then added to the beads and 50 ml of 25% glutardialdehyde is added. The beads are maintained at 7° to 8° C. and stirred occasionally over 1 hour. After 1 hour, the beads are transferred to a sieve and are rinsed with water to remove excess glutardialdehyde.

The same procedure is followed with the second ½ of the mixture until all the beads have been formed and cross-linked. All beads are then mixed together and dewatering is performed as described in Example 29.

EXAMPLE 33

Selection of Organisms for Lactic Acid Production

D-Lactic Acid

*Bacillus laevolactis* was chosen as a potential candidate for the production of D-Lactic Acid. *B. laevolactis* however is positive for protease production. Therefore the first selection of this organism was to find a strain that was protease negative or one that produced minimal protease.

*B. laevolactis* was grown in Bacillus Broth. Organisms were plated on Bacillus Medium and after 24 hours, individual colonies were transferred to 15% (w/w) Gelatin plates and allowed to incubate for 24 hours. After incubation, any colonies producing little protease were recovered and the process was repeated four (4) times. After the fourth generation of low protease producing Bacillus was isolated, the colonies were plated on Bacillus Medium and exposed to UV light. These colonies were then plated on 15% Gelatin and the process was repeated five (5) times until two colonies were isolated that did not liquify 15% Gelatin in 24 hours. 12% Gelatin plates were then used to verify negative protease production. These strains were then grown in Bacillus Broth and designated as MFG1 and MFG2.

These strains were used to inoculate flasks containing Bacillus Broth (½ strength) plus 15% (w/w) glucose. MFG1 produced 7% Lactic Acid (w/w) and MFG2 produced 5.6% (w/w) Lactic Acid in 96 hours.

L-Lactic Acid

Several organisms were screened for L-Lactic Acid production. *Lactobacillus casei, L. plantarum*, and Pediococcus species all proved to be heterofermentative organisms. *Rhizopus orysae* and *Lactobacillus delbrueckii* were found to be the most likely candidates for high lactic acid production combined with high purity.

*L. delbrueckii* has undergone eleven generations of selection to yield thirty-eight possible candidates for lactic acid production. The tenth generation of *L. delbrueckii* was exposed to UV light and two colonies from the third generation after UV light have been chosen for immobilization and designated as LA103C and LA103F.

EXAMPLE 34

*Bacillus laevolactis* strain MFG1 was immobilized as outlined in Example 31. The beads produced were of uniform size and shape. The immobilized organisms were allowed to ferment glucose for 96 hours in a shake flask and produced 11.1% (w/w) lactic acid when fed with enough glucose to produce 15%.

EXAMPLE 35

*Lactobacillus delbrueckii* strains LA104F and LA103C were immobilized using the same procedure as used in Example 31. LA103F produced 12.4% (w/w) lactic acid and LA103C produced 14.6% (w/w) lactic acid after 96 hours in shake flasks. Both strains produced less than 0.5% (v/v) ethanol.

Various modifications of the products and method of the invention may be made without departing from the spirit or scope thereof and it is to be understood that the invention is intended to be limited only as defined in the appended claims.

What we claim is:

1. An immobilized water-insoluble biocatalyst in particulate form consisting essentially of living cells in a gelling agent comprising gelatin which is cross-linked with a cross-linking agent, the biocatalyst being further characterized in that at least part of the water is removed from the cross-linked particles to give a dry matter content of at least 15%.

2. A biocatalyst according to claim 1 wherein the living cells are selected from the group consisting of yeasts, bacteria and plant cells, or mixtures thereof.

3. A biocatalyst according to claim 1 wherein the living cells are dispersed in conjunction with one or more enzymes which are compatible with the living cells and the gelling agent.

4. A biocatalyst according to claim 3 wherein the enzymes are selected from the group consisting of amyloglucosidase, lactase, maltase, amylase, glucose isomerase, pullulanase, invertase, lipase, esterase, glucose oxidase, glucose dehydrogenase, cellulase, hemicellulase and xylanase.

5. A biocatalyst according to claim 1 wherein the living cells are an ethanol sensitive strain of S. cerevisiae having a D-value (the time required to kill 90% of the living cells at 58° C.) of more than 25 seconds.

6. A biocatalyst according to claim 1 which comprises viable S. cerevisiae cells optionally in conjunction with amyloglucosidase dispersed in cross-linked gelatin.

7. A biocatalyst according to claim 1 wherein the living cells are a thermophilic strain of S. cerevisiae capable of sustained growth in yeast extract/peptone/glucose at a temperature in excess of 40° C.

8. A biocatalyst according to claim 7 wherein the thermotolerant strain is S. cerevisiae CBS 252.86.

9. A biocatalyst according to claim 6 wherein the viable cells are of the strain S. cerevisiae CBS 253.86.

* * * * *

UNITED STATES PATENT AND TRADEMARK OFFICE
CERTIFICATE OF CORRECTION

PATENT NO. : 5,137,818
DATED : August 11, 1992
INVENTOR(S) : Abraham Harder, et al It is certified that error appears in the above-indentified patent and that said Letters Patent is hereby corrected as shown below:

On the title page item [30], insert the following:

International
PCT Application No. NL 86/00039

Signed and Sealed this

Thirty-first Day of January, 1995

Attest:

BRUCE LEHMAN

*Attesting Officer*   *Commissioner of Patents and Trademarks*